United States Patent
Autry et al.

(10) Patent No.: US 6,995,171 B2
(45) Date of Patent: Feb. 7, 2006

(54) BICYCLIC PYRIMIDINE AND PYRIMIDINE DERIVATIVES USEFUL AS ANTICANCER AGENTS

(75) Inventors: Christopher Autry, New London, CT (US); Michael J. Luzzio, Noank, CT (US); Matthew A. Marx, Waterford, CT (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 46 days.

(21) Appl. No.: 10/479,655

(22) PCT Filed: Jun. 20, 2002

(86) PCT No.: PCT/US02/19830

§ 371 (c)(1),
(2), (4) Date: Dec. 1, 2003

(87) PCT Pub. No.: WO03/000194

PCT Pub. Date: Jan. 3, 2003

(65) Prior Publication Data

US 2004/0171590 A1   Sep. 2, 2004

Related U.S. Application Data

(60) Provisional application No. 60/299,879, filed on Jun. 21, 2001.

(51) Int. Cl.
*A61K 31/4365* (2006.01)
*C07D 495/04* (2006.01)

(52) U.S. Cl. ............. 514/301; 546/114; 544/127; 544/362; 514/233.8; 514/253

(58) Field of Classification Search ............. 514/301, 514/253, 233.8; 546/114; 544/127, 362
See application file for complete search history.

(56) References Cited

U.S. PATENT DOCUMENTS

| | | | |
|---|---|---|---|
| 4,710,506 A | * | 12/1987 | Davies et al. ............. 514/301 |
| 5,587,458 A | | 12/1996 | King et al. |
| 5,747,498 A | | 5/1998 | Schnur et al. |
| 5,792,783 A | | 8/1998 | Tang et al. |
| 5,834,504 A | | 11/1998 | Begley et al. |
| 5,861,510 A | | 1/1999 | Piscopio et al. |
| 5,863,949 A | | 1/1999 | Robinson et al. |
| 5,877,305 A | | 3/1999 | Huston et al. |
| 5,883,113 A | | 3/1999 | Tang et al. |
| 5,886,020 A | | 3/1999 | Tang et al. |
| 6,071,935 A | | 6/2000 | Lyssikatos |
| 6,225,318 B1 | | 5/2001 | Sobolov-Jaynes et al. |
| 6,284,764 B1 | | 9/2001 | Kath et al. |
| 6,465,449 B1 | | 10/2002 | Kath et al. |
| 6,682,736 B1 | | 1/2004 | Hanson et al. |

FOREIGN PATENT DOCUMENTS

| | | |
|---|---|---|
| EP | 0239362 | 12/1991 |
| EP | 606046 | 7/1994 |
| EP | 780386 | 6/1997 |
| EP | 0818442 | 1/1998 |
| EP | 931788 | 7/1999 |
| EP | 952148 | 10/1999 |
| EP | 1044578 | 5/2000 |
| EP | 1081138 | 3/2001 |
| WO | WO 90/05719 | 5/1990 |
| WO | WO 95/19774 | 7/1995 |
| WO | WO 95/19970 | 7/1995 |
| WO | WO 95/21613 | 8/1995 |
| WO | WO 95/23141 | 8/1995 |
| WO | WO 96/27583 | 9/1996 |
| WO | WO 96/30347 | 10/1996 |
| WO | WO 96/33172 | 10/1996 |
| WO | WO 96/40142 | 12/1996 |
| WO | WO 97/13760 | 4/1997 |

(Continued)

OTHER PUBLICATIONS

Compounds with RN 65075-96-9 and RN 99429-85-3.*

(Continued)

*Primary Examiner*—Charanjit S. Aulakh
(74) *Attorney, Agent, or Firm*—Matthew J. Pugmire; Bryan C. Zielinski

(57) ABSTRACT

The invention relates to compounds of the formulas 1 and 2

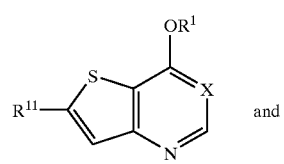

and

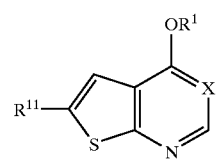

and to prodrugs thereof, pharmaceutically acceptable salts or solvates of said compounds or said prodrugs, wherein X, $R^1$ and $R^{11}$ are as defined herein. The invention also relates to pharmaceutical compositions containing the compounds of formulas 1 and 2 and to methods of treating hyperproliferative disorders in a mammal by administering the compounds of formulas 1 and 2.

21 Claims, No Drawings

FOREIGN PATENT DOCUMENTS

| | | |
|---|---|---|
| WO | WO 97/13771 | 4/1997 |
| WO | WO 97/22596 | 6/1997 |
| WO | WO 97/32856 | 9/1997 |
| WO | WO 97/49688 | 12/1997 |
| WO | WO 98/02434 | 1/1998 |
| WO | WO 98/02437 | 1/1998 |
| WO | WO 98/02438 | 1/1998 |
| WO | WO 98/03516 | 1/1998 |
| WO | WO 98/07697 | 2/1998 |
| WO | WO 98/14451 | 4/1998 |
| WO | WO 98/23613 | 6/1998 |
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 98/50356 | 11/1998 |
| WO | WO 98/54093 | 12/1998 |
| WO | WO 99/07675 | 2/1999 |
| WO | WO 99/10349 | 3/1999 |
| WO | WO 99/16755 | 4/1999 |
| WO | WO 99/24440 | 5/1999 |
| WO | WO 99/29667 | 6/1999 |
| WO | WO 99/35132 | 7/1999 |
| WO | WO 99/35146 | 7/1999 |
| WO | WO 99/52889 | 10/1999 |
| WO | WO 99/52910 | 10/1999 |
| WO | WO 99/61422 | 12/1999 |
| WO | WO 99/62890 | 12/1999 |
| WO | WO 00/74681 | 12/2000 |
| WO | WO 00/38665 | 7/2001 |

OTHER PUBLICATIONS

Barker, John M., et al., "Thienopyridines. Part 5. Carbon-13 N.m.r. Spectra of Some Thieno[3,2-b]pyridines, and Some Further Transformations in the Series," *J. Chem. Research*, 1984, 84-85.

Barker, John M., et al., "Thienyl Analogues of the Alkaloids. Part 3. Analogues of Echinorine and Echinopsine; a Convenient Synthesis of Thieno[3,2-b]pyridines," *J. Chem. Research*, 1978, 393.

Cao, Y., et al., "Heterodimers of Placenta Growth Factor/Vascular Endothelial Growth Factor", *J. Biol. Chem.*, 1996, 3154-3162, vol. 271, No. 6.

Corbett, T.H., et al., "A Mouse Colon-tumor Model for Experimental Therapy," *Cancer Chemotherapy Reporter (Part 2).*, 1975, 169-186, vol. 5.

Corbett, T.H., et al., "Tumor Induction Relationships in Development of Transplantable Cancers of the Colon in Mice for Chemotherapy Assays, with a Note on Carcinogen Structure," *Cancer Research*, 1975, 2434-2439, vol. 35.

Fleisher, et al., "Improved Oral Drug Delivery: Solubility Limitations Overcome by the Use of Prodrugs," *Advanced Drug Delivery Reviews*, 1996, 115-130, vol. 19.

Furniss, B.S., et al., *Vogel's Textbook of Practical Organic Chemistry*, Fifth Edition, 1996, Longman, Harlow, England.

Geran, R.I., et al., "Protocols for Screening Chemical Agents and Natural Products Aganist Animal Tumors and Other Biological Systems," *Cancer Chemotherapy Reporter*, Third Edition, 1972, pp. 1-104, vol. 3.

Gill, G.N., et al., "[7] Purification of Functionally Active Epidermal Growth Factor Receptor Protein Using a Competitive Antagonist Monoclonal Antibody and Competitve Elution with Epidermal Growth Factor," *Methods in Enzymology*, 1987, 82-86, vol. 146.

Greene, T.W., et al., *Protective Groups in Organic Synthesis*, Second Edition, 1991, John Wiley & Sons, New York.

Katritzky, et al., *Comprehensive Heterocyclic Chemistry II*, 1996, vols. 5, 6 and 7, Elsevier Science Ltd., Oxford.

Klemm, L.H., et al., "Chemistry of Thienopyridines. XXIV. Two Transformations of Thieno [2,3-b]pyrimidine 7-Oxide (1)," *J. Heterocyclic Chem.*, 1976, 1197-1200, vol. 13.

Miyaura, et al., "Palladium-Catalyzed Cross-Coupling Reactions of Organoboron Compounds," *Chem. Rev.*, 1995, 2457-2483, vol. 95.

Posner, et al., "Kinetic Model of the Epidermal Growth Factor (EGF) Receptor Tyrosine Kinase and a Possible Mechanism of Its Activation by EGF," *Journal of Biological Chemistry*, 1992, 20638-20647, vol. 267, No. 29.

Remington, et al., *Remington's Pharmaceutical Sciences*, $15^{th}$ Ed., 1975, Mack Publishing Co., Easter, PA.

Robinson, et al., "Discovery of the Hemifumarate and (α-L-Alanyloxy)methyl Ether as Prodrugs of Antirheumatic Oxindole: Prodrugs for the Enolic OH Group," *J. Med. Chem.*, 1996, 10-18, vol. 39, No. 1.

Sumpter, et al., "Hetercyclic Compounds with Indole and Carbazole Systems," *The Chemistry of Heterocyclic Compounds*, 1954, Interscience Publishers, New York.

Waltenberger, et al., "Different Signal Transduction Properties of KDR and Flt1, Two Receptors for Vascular Endothelial Growth Factor," *J. Biol. Chem.*, 1994, 26988-26995, vol. 269, No. 43.

* cited by examiner

BICYCLIC PYRIMIDINE AND PYRIMIDINE DERIVATIVES USEFUL AS ANTICANCER AGENTS

This application claims benefit to international application No. PCT/US02/19830, filed on Jun. 20, 2002, published in English, which claims the benefit of U.S. provisional application No. 60/299,879, filed on Jun. 21, 2001.

BACKGROUND OF THE INVENTION

This invention relates to novel bicyclic pyridine and pyrimidine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Compounds that are useful in the treatment of hyperproliferative diseases are also disclosed in the following patents and applications: PCT international patent application publication number WO 00/38665 (published Jul. 6, 2001), PCT international patent application publication number WO 97/49688 (published Dec. 31, 1997), PCT international patent application publication number WO 98/23613 (published Jun. 4, 1998), U.S. patent application Ser. No. 08/953,078 (filed Oct. 17, 1997), U.S. Pat. No. 6,071,935 issued Jun. 6, 2000, PCT international patent application publication number WO 96/30347 (published Oct. 3, 1996), PCT international patent application publication number WO 96/40142 (published Dec. 19,1996), PCT international patent application publication number WO 97/13771 (published Apr. 17, 1997), and PCT international patent application publication number WO 95/23141 (published Aug. 31, 1995). The foregoing patent and applications are incorporated herein by reference in their entirety.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate a specific tyrosine residue in proteins and hence to influence cell proliferation. The foregoing tyrosine kinases may be classified as growth factor receptor (e.g. EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995).

It is known that polypeptide growth factors such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995). Agents, such as the compounds of the present invention, that are capable of binding to or modulating the KDR/FLK-1 receptor may be used to treat disorders related to vasculogenesis or angiogenesis such as diabetes, diabetic retinopathy, hemangioma, glioma, melanoma, Kaposi's sarcoma and ovarian, breast, lung, pancreatic, prostate, colon and epidermoid cancer.

SUMMARY OF THE INVENTION

The present invention relates to compounds of the formulas 1 and 2

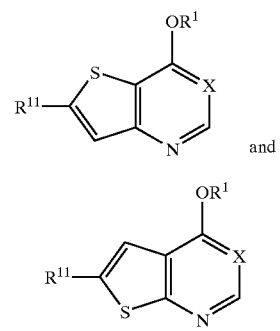

and to prodrugs thereof, pharmaceutically acceptable salts or solvates of said compounds and said prodrugs, wherein X is CH or N;

$R^1$ is H, $C_1$–$C_6$ alkyl, —C(O)($C_1$–$C_6$ alkyl), $C_6$–$C_{10}$ aryl or 5 to 13 membered heterocyclic, wherein said $C_6$–$C_{10}$ aryl and 5 to 13 membered heterocyclic groups are optionally substituted by 1 to 5 $R^5$ substituents;

each $R^5$ is independently selected from halo, cyano, nitro, trifluoromethoxy, trifluoromethyl, azido, —C(O)$R^8$, —C(O)OR$^8$, —OC(O)$R^8$, —OC(O)OR$^8$, —NR$^6$C(O)$R^7$, —C(O)NR$^6$R$^7$, —NR$^6$R$^7$, —OR$^9$, —SO$_2$NR$^6$R$^7$, $C_1$–$C_6$ alkyl, —(CH$_2$)$_j$O(CH$_2$)$_q$NR$^6$R$^7$, —(CH$_2$)$_t$O(CH$_2$)$_q$OR$^9$, —(CH$_2$)$_t$OR$^9$, —S(O)$_j$($C_1$–$C_6$ alkyl), —(CH$_2$)$_t$($C_6$–$C_{10}$ aryl), —(CH$_2$)$_t$(5 to 10 membered heterocyclic), —C(O)(CH$_2$)$_t$($C_6$–$C_{10}$ aryl), —(CH$_2$)$_t$O(CH$_2$)$_j$($C_6$–$C_{10}$ aryl), —(CH$_2$)$_t$O(CH$_2$)$_q$(5 to 10 membered heterocyclic), —C(O)(CH$_2$)$_t$(5 to 10 membered heterocyclic), —(CH$_2$)$_j$NR$^7$(CH$_2$)$_q$NR$^8$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_t$O(CH$_2$)$_q$OR$^9$, —(CH$_2$)$_j$NR$^7$(CH$_2$)$_q$S(O)$_j$($C_1$–$C_6$ alkyl), —(CH$_2$)$_j$NR$^7$(CH$_2$)$_t$R$^6$, —SO$_2$ $(CH_2)_t(C_6-C_{10}$ aryl), and $—SO_2(CH_2)_t(5$ to 10 membered heterocyclic), wherein j is an integer from 0 to 2, t is an integer from 0 to 6, q is an integer from 2 to 6, the $—(CH_2)_q—$ and $—(CH_2)_t—$ moieties of the foregoing $R^5$ groups optionally include a carbon-carbon double or triple bond where t is an integer between 2 and 6, and the alkyl, aryl and heterocyclic moieties of the foregoing $R^5$ groups are optionally substituted by 1 to 3 substituents independently selected from halo, cyano, nitro, trifluoromethyl, azido, $—C(O)R^8$, $—C(O)OR^8$, $—OC(O)R^8$, $—OC(O)OR^8$, $—NR^6C(O)R^7$, $—C(O)NR^6R^7$, $—(CH_2)_tNR^6R^7$, $C_1-C_6$ alkyl, $—(CH_2)_t(C_6-C_{10}$ aryl), $—(CH_2)_t(5$ to 10 membered heterocyclic), $—(CH_2)_tO(CH_2)_qOR^9$, and $—(CH_2)_tOR^9$, wherein t is an integer from 0 to 6 and q is an integer from 2 to 6;

each $R^6$ and $R^7$ is independently selected from H, $C_1-C_6$ alkyl, $—(CH_2)_t(C_6-C_{10}$ aryl), $—(CH_2)_t(5$ to 10 membered heterocyclic), $—(CH_2)_tO(CH_2)_qOR^9$, and $—(CH_2)_tOR^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, nitro, trifluoromethyl, azido, $—C(O)R^8$, $—C(O)OR^8$, $—CO(O)R^8$, $—OC(O)OR^8$, $—NR^9C(O)R^{10}$, $—C(O)NR^9R^{10}$, $—NR^9R^{10}$, $C_1-C_6$ alkyl, $—(CH_2)_t(C_6-C_{10}$ aryl), $—(CH_2)_t(5$ to 10 membered heterocyclic), $—(CH_2)_tO(CH_2)_qOR^9$, and $—(CH_2)_tOR^9$, wherein t is an integer from 0 to 6 and q is an integer from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1-C_{10}$ alkyl, $—(CH_2)_t(C_6-C_{10}$ aryl), and $—(CH_2)_t(5$ to 10 membered heterocyclic), wherein t is an integer from 0 to 6;

each $R^9$ and $R^{10}$ is independently selected from H and $C_1-C_6$ alky; and, $R^{11}$ is H, $C_1-C_6$ alky, $—C(O)NR^{12}R^{13}$, $—C(O)(C_6-C_{10}$ aryl), $—(CH_2)_t(C_6-C_{10}$ aryl), $—(CH_2)_t(5$ to 10 membered heterocyclic), $—(CH_2)_tNR^{12}R^{13}$, $—SO_2NR^{12}R^{13}$ and $—CO_2R^{12}$, wherein t is an integer from 0 to 6, wherein said $R^{11}$ groups $C_1-C_6$ alkyl, $—C(O)(C_6-C_{10}$ aryl), $—(CH_2)_t(C_6-C_{10}$ aryl), and $—(CH_2)_t(5$ to 10 membered heterocyclic) are optionally substituted by 1 to 5 $R^5$ groups, and wherein each $R^{12}$ and $R^{13}$ is independently selected from H, $C_1-C_6$ alkyl, $—(CH_2)_t(C_3-C_{10}$ cycloalkyl), $—(CH_2)_t(C_6-C_{10}$ aryl), $—(CH_2)_t(5$ to 10 membered heterocyclic), $—(CH_2)_tO(CH_2)_q OR^9$, and $—(CH_2)_tOR^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, and said rings are optionally substituted by 1 to 5 $R^5$ substituents, with the proviso $R^{12}$ and $R^{13}$ are not both bonded to the nitrogen directly through an oxygen.

In one preferred embodiment of the compound of formula 1 $R^{11}$ is $—(CH_2)_t(5$ to 10 membered heterocyclic), $—C(O)NR^{12}R^{13}$, $—(CH_2)_tNR^{12}R^{13}$, $—SO_2NR^{12}R^{13}$ and $—CO_2R^{12}$, wherein t is an integer from 0 to 6, wherein said $R^{11}$ group $—(CH_2)_t(5$ to 10 membered heterocyclic) is optionally substituted by 1 to 5 $R^5$ groups and wherein each $R^{12}$ and $R^{13}$ is independently selected from H, $C_1-C_8$ alkyl, $—(CH_2)_t(C_3-C_{10}$ cycloalkyl), $—(CH_2)_t(C_6-C_{10}$ aryl), $—(CH_2)_t(5$ to 10 membered heterocyclic), $—(CH_2)_tO(CH_2)_q OR^9$, $—(CH_2)_tOR^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

In another preferred embodiment of the compound of formula 1 $R^{11}$ is $—(CH_2)_t(5$ to 10 membered heterocyclic), $—C(O)NR^{12}R^{13}$, $—SO_2NR^{12}R^{13}$ and $—CO_2R^{12}$, wherein t is an integer from 0 to 6, wherein said $R^{11}$ group $—(CH_2)_t(5$ to 10 membered heterocyclic) is optionally substituted by 1 to 5 $R^5$ groups and wherein each $R^{12}$ and $R^{13}$ is independently selected from H, $C_1-C_6$ alkyl, $—(CH_2)_t(C_3-C_{10}$ cycloalkyl), $—(CH_2)_t(C_6-C_{10}$ aryl), $—(CH_2)_t(5$ to 10 membered heterocyclic), $—(CH_2)_tO(CH_2)_qOR^9$, $—(CH_2)_tOR^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

In another preferred embodiment of the compound of formula 1 $R^{11}$ is $—(CH_2)_t(5$ to 10 membered heterocyclic), and $—C(O)NR^{12}R^{13}$, wherein t is an integer from 0 to 6, wherein said $R^{11}$ group $—(CH_2)_t(5$ to 10 membered heterocyclic) is optionally substituted by 1 to 5 $R^5$ groups and wherein each $R^{12}$ and $R^{13}$ is independently selected from H, $C_1-C_6$ alkyl, $—(CH_2)_t(C_3-C_{10}$ cycloalkyl), $—(CH_2)_t(C_6-C_{10}$ aryl), $—(CH_2)_t(5$ to 10 membered heterocyclic), $—(CH_2)_tO(CH_2)_qOR^9$, $—(CH_2)_tOR^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5-C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

In another preferred embodiment of the compound of formula 1 $R^{11}$ is $—C(O)NR^{12}R^{13}$, wherein $R^{12}$ and $R^{13}$ are independently selected from H, $C_1-C_6$ alkyl, $—(CH_2)_t(C_3-C_{10}$ cycloalkyl), $—(CH_2)_t(C_6-C_{10}$ aryl), $—(CH_2)_t(5$ to 10 membered heterocyclic), $—(CH_2)_tO(CH_2)_qOR^9$, $—(CH_2)_tOR^9$, wherein t is an integer from 0 to 6, q is an integer from 2 to 6, and the alkyl, aryl and heterocyclic moieties of the foregoing $R^{12}$ and $R^{13}$ groups are optionally substituted by 1 to 3 substituents independently selected from R$^5$ or R$^{12}$ and R$^{13}$ are taken together with the nitrogen to which they are attached to form a C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 R$^5$ substituents, with the proviso R$^{12}$ and R$^{13}$ are not both bonded to the nitrogen directly through an oxygen.

In another preferred embodiment of the compound of formula 1 R$^{11}$ is —C(O)NR$^{12}$R$^{13}$, wherein R$^{12}$ and R$^{13}$ are taken together with the nitrogen to which they are attached to form a C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 R$^5$ substituents.

In another preferred embodiment of the compound of formula 1 R$^{11}$ is —C(O)NR$^{12}$R$^{13}$ wherein R$^{12}$ and R$^{13}$ are taken together with the nitrogen to which they are attached to form a pyrrolidinyl, piperidinyl, piperazinyl, morpholinyl, thiomorpholinyl, isoquinolinyl, or dihydroisoquinolinyl ring, wherein said pyrrolidinyl, piperidinyl, piperazinyl, morpholinyl, thiomorpholinyl, isoquinolinyl, or dihydroisoquinolinyl ring are optionally substituted by 1 to 5 R$^5$ substituents.

In another preferred embodiment of the compound of formula 1 R$^{11}$ is —C(O)NR$^{12}$R$^{13}$, wherein R$^{12}$ and R$^{13}$ are taken together with the nitrogen to which they are attached to form a pyrrolidinyl, piperidinyl, piperazinyl, morpholinyl, or thiomorpholinyl ring, wherein said pyrrolidinyl, piperidinyl, piperazinyl, morpholinyl, or thiomorpholinyl ring are optionally substituted by 1 to 5 R$^5$ substituents.

In another preferred embodiment of the compound of formula 1 R$^{11}$ is —C(O)NR$^{12}$R$^{13}$, wherein R$^{12}$ and R$^{13}$ are taken together with the nitrogen to which they are attached to form a pyrrolidinyl or piperidinyl ring, wherein said pyrrolidinyl or piperidinyl ring are optionally substituted by 1 to 5 R$^5$ substituents.

In another preferred embodiment of the compound of formula 1 R$^{11}$ is —C(O)NR$^{12}$R$^{13}$ wherein R$^{12}$ and R$^{13}$ are taken together with the nitrogen to which they are attached to form a pyrrolidinyl ring, wherein said pyrrolidinyl is optionally substituted by 1 to 5 R$^5$ substituents.

In another preferred embodiment of the compound of formula 1 R$^{11}$ is —C(O)NR$^{12}$R$^{13}$, wherein R$^{12}$ and R$^{13}$ are taken together with the nitrogen to which they are attached to form a pyrrolidin-1-yl ring, wherein said pyrrolidin-1-yl is optionally substituted by 1 to 5 R$^5$ substituents.

In another preferred embodiment of the compound of formula 1 R$^{11}$ is —(CH$_2$)$_t$(5 to 10 membered heterocyclic) group, wherein t is an integer from 0 to 6, said —(CH$_2$)$_t$(5 to 10 membered heterocyclic) group is optionally substituted by 1 to 5 R$^5$ groups.

In another preferred embodiment of the compound of formula 1 R$^{11}$ is —(CH$_2$)$_t$(5–8 membered heterocyclic) group, wherein t is an integer from 0 to 6, said —(CH$_2$)$_t$(5–8 membered heterocyclic) group is optionally substituted by 1 to 5 R$^5$ groups.

In another preferred embodiment of the compound of formula 1 R$^{11}$ is —(CH$_2$)$_t$(5 or 6 membered heterocyclic) group, wherein t is an integer from 0 to 6, said —(CH$_2$)$_t$(5 or 6 membered heterocyclic) group is optionally substituted by 1 to 5 R$^5$ groups.

In another preferred embodiment of the compound of formula 1 R$^{11}$ is —(CH$_2$)$_t$(5 membered heterocyclic) group, wherein t is an integer from 0 to 6, said —(CH$_2$)$_t$(5 membered heterocyclic) group is optionally substituted by 1 to 5 R$^5$ groups.

In another e preferred embodiment the compound of formula 1 R$^{11}$ is —(CH$_2$)$_t$thiazolyl, wherein t is an integer from 0 to 6, said —(CH$_2$)$_t$thiazolyl is optionally substituted by 1 to 5 R$^5$ groups.

Other preferred compounds include those of formula 1 wherein R$^1$ is phenyl optionally substituted by 1 to 5 R$^5$ substituents, or R$^1$ is a group of the formula

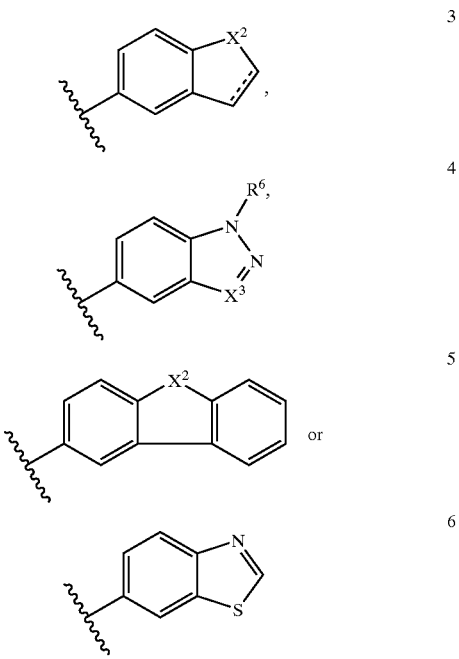

wherein X$^2$ is —S— or —N(R$^6$)—, X$^3$ is N or CH, the dashed line in formula 3 represents an optional double bond, and the above R$^1$ groups of formulas 3 and 5 are optionally substituted by 1 to 5 R$^5$ substituents and the R$^1$ groups of formulas 4 and 6 are optionally substituted by 1 to 3 R$^5$ substituents. Specifically preferred compounds include those wherein R$^1$ is a group of formula 3 above wherein said group is optionally substituted by 1 to 5 R$^5$ substituents.

Specific embodiments of the present invention include the following compounds:

(3R)-(3-methoxy-pyrrolidin-1-yl)-[7-(2-methyl-1H-indol-5-yloxy)-thieno[3,2-b]pyridin-2-yl]-methanone;
(3S)-(3-Methoxy-pyrrolidin-1-yl)-[7-(2-methyl-1H-indol-5-yloxy)-thieno[3,2-b]pyridin-2-yl]-methanone;
(3R,4R)-(3,4-Dimethoxy-pyrrolidin-1-yl)-[7-(2-methyl-1H-indol-5-yloxy)-thieno[3,2-b]pyridin-2-yl]-methanone;
meso-(3,4-Dimethoxy-pyrrolidin-1-yl)-[7-(2-methyl-1H-indol-5-yloxy)-thieno[3,2-b]pyridin-2-yl]-methanone;
(3S,4S)-(3,4-Dimethoxy-pyrrolidin-1-yl)-[7-(2-methyl-1H-indol-5-yloxy)-thieno[3,2-b]pyridin-2-yl]-methanone;
(R)-(2-Hydroxymethyl-pyrrolidin-1-yl)-[7-(2-methyl-1H-indol-5-yloxy)-thieno[3,2-b]pyridin-2-yl]-methanone;
(S)-(2-Hydroxymethyl-pyrrolidin-1-yl)-[7-(2-methyl-1H-indol-5-yloxy)-thieno[3,2-b]pyridin-2-yl]-methanone;
(2R)-(2-Methoxymethyl-pyrrolidin-1-yl)-[7-(2-methyl-1H-indol-5-yloxy)-thieno[3,2-b]pyridin-2-yl]-methanone;

(2S)-(2-Methoxymethyl-pyrrolidin-1-yl)-[7-(2-methyl-1H-indol-5-yloxy)-thieno[3,2-b]pyridin-2-yl]-methanone;
(R)-[7-(1-Ethyl-2-methyl-1H-indol-5-yloxy)-thieno[3,2-b]pyridin-2-yl]-(2-methoxymethyl-pyrrolidin-1-yl)-methanone;
(2R)-[7-(1,2-Dimethyl-1H-indol-5-yloxy)-thieno[3,2-b]pyridin-2-yl]-(2-methoxymethyl-pyrrolidin-1-yl)-methanone;
(2R)-1-{5-[2-(2-Methoxymethyl-pyrrolidine-1-carbonyl)-thieno[3,2-b]pyridin-7-yloxy]-2-methyl-indol-1-yl}-ethanone;
(2R)-[7-(1-Methanesulfonyl-2-methyl-1H-indol-5-yloxy)-thieno[3,2-b]pyridin-2-yl]-(2-methoxymethyl-pyrrolidin-1-yl)-methanone;
2-(3-Methyl-3H-imidazol-4-yl)-7-(2-methyl-1H-indol-5-yloxy)-thieno[3,2-b]pyridine;
2-(1-Methyl-1H-imidazol-2-yl)-7-(2-methyl-1H-indol-5-yloxy)-thieno[3,2-b]pyridine;
2-{2-[7-(2-Methyl-1H-indol-5-yloxy)-thieno[3,2-b]pyridin-2-yl]-thiazol-4-yl}-propan-2-ol;
2-{2-[7-(2-Methyl-quinolin-6-yloxy)-thieno[3,2-b]pyridin-2-yl]-thiazol-4-yl}-propan-2-ol;
2-{2-[7-(Quinolin-6-yloxy)-thieno[3,2-b]pyridin-2-yl]-thiazol-4-yl}-propan-2-ol;
2-{2-[7-(1-Methyl-5-trifluoromethyl-1H-pyrazol-3-yloxy)-thieno[3,2-b]pyridin-2-yl]-thiazol-4-yl}-propan-2-ol;
{4-Methyl-2-[7-(2-methyl-1H-indol-5-yloxy)-thieno[3,2-b]pyridin-2-yl]-thiazol-5-yl}-4-methyl-piperazin-1-yl)-methanone;
2-Methyl-5-{2-[4-methyl-5-(4-methyl-piperazine-1-carbonyl)-thiazol-2-yl]-thieno[3,2-b]pyridin-7-yloxy}-1H-indole-3-carbonitrile;
{4-Methyl-2-[7-(5-phenyl-1H-pyrazol-3-yloxy)-thieno[3,2-b]pyridin-2-yl]-thiazol-5-yl}-morpholin-4-yl-methanone;
(2-{7-[5-(4-Fluoro-phenyl)-1H-pyrazol-3-yloxy]-thieno[3,2-b]pyridin-2-yl}-4-methyl-thiazol-5-yl)-(4-methyl-piperazin-1-yl)-methanone;
2-{(7-[5-(4-Methoxy-phenyl)-1H-pyrazol-3-yloxy]-thieno[3,2-b]pyridin-2-yl}-4-methyl-thiazol-5-yl)-(4-methyl-piperazin-1-yl)-methanone; and pharmaceutically acceptable salts and solvates of said compounds.

The present invention also relates to intermediate compounds of the formulas 25 and 26

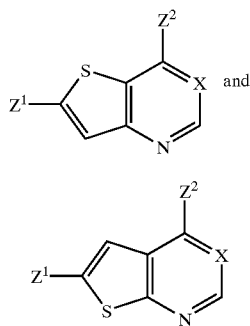

and to pharmaceutically acceptable salts thereof, wherein:
$Z^1$ is halo, —$CO_2H$, —$CONH_2$, —$CSNH_2$ and $Z^2$ is —$OR^1$; or
$Z^1$ is $R^{11}$ and $Z^2$ is halo; or
$Z^1$ and $Z^2$ are each independently halo;
X is N or CH; and wherein $R^1$ and $R^{11}$ are as defined for said compounds of formulas 1 and 2.

The above intermediates of formulas 25 and 26 may be used to prepare the above compounds of formulas 1 and 2.

This invention also relates to pharmaceutical compositions containing and methods for treating abnormal cell growth through administering prodrugs of compounds of the formulas 1 and 2. Compounds of formulas 1 and 2 having free amino, amido, hydroxy or carboxylic groups can be converted into prodrugs.

The invention also relates to a pharmaceutical composition for the treatment of a hyperproliferative disorder in a mammal which comprises a therapeutically effective amount of a compound of formula 1 or 2, or prodrugs thereof, pharmaceutically acceptable salts or solvates of said compounds and said prodrugs, and a pharmaceutically acceptable carrier. In one embodiment, said pharmaceutical composition is for the treatment of cancer such as brain, lung, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula 1 or 2, or prodrugs thereof, pharmaceutically acceptable salts or solvates of said compounds and said prodrugs, and a pharmaceutically acceptable carrier.

The invention also relates to a pharmaceutical composition for the prevention of blastocyte implantation in a mammal which comprises a therapeutically effective amount of a compound of formula 1 or 2, or prodrugs thereof, pharmaceutically acceptable salts or solvates of said compounds and said prodrugs, and a pharmaceutically acceptable carrier.

The invention also relates to a pharmaceutical composition for treating a disease related to vasculogenesis or angiogenesis in a mammal which comprises a therapeutically effective amount of a compound of formula 1 or 2, or prodrugs thereof, pharmaceutically acceptable salts or solvates of said compounds and said prodrugs, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula 1 or 2, or prodrugs thereof, pharmaceutically acceptable salts or solvates of said compounds and said prodrugs. In one embodiment, said method relates to the treatment of cancer such as brain, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula 1 or 2, or prodrugs thereof, pharmaceutically acceptable salts or solvates of said compounds and said prodrugs, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula 1 or 2, or prodrugs thereof, pharmaceutically acceptable salts or solvates of said compounds and said prodrugs.

The invention also relates to a method of preventing blastocyte implantation in a mammal which comprises administering to said mammal a therapeutically effective amount of a compound of formula 1 or 2, or prodrugs thereof, pharmaceutically acceptable salts or solvates of said compounds and said prodrugs.

The invention also relates to a method of treating diseases related to vasculogenesis or angiogenesis in a mammal which comprises administering to said mammal an effective amount of a compound of formula 1 or 2, or prodrugs thereof, pharmaceutically acceptable salts or solvates of said compounds and said prodrugs. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with the compounds of formulas 1 and 2, and prodrugs thereof, pharmaceutically acceptable salts or solvates of said compounds and said prodrugs, according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to a pharmaceutical composition for inhibiting abnormal cell growth in a mammal, including a human, comprising an amount of a compound of the formula 1 or 2 as defined above, or prodrug thereof, pharmaceutically acceptable salt or solvate of said compound and said prodrug, that is effective in inhibiting farnesyl protein transferase, and a pharmaceutically acceptable carrier.

This invention also relates to a pharmaceutical composition for inhibiting abnormal cell growth in a mammal which comprises an amount of a compound of formula 1 or 2, or prodrug thereof, pharmaceutically acceptable salt or solvate of said compound and said prodrug, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

This invention further relates to a method for inhibiting abnormal cell growth in a mammal which method comprises administering to the mammal an amount of a compound of formula 1 or 2, or prodrug thereof, pharmaceutically acceptable salt or solvate of said compound and said prodrug, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula 1 or 2 can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula 1 or 2 or prodrug thereof, pharmaceutically acceptable salt or solvate of said compound and said prodrug, which amount is effective in sensitizing abnormal cells to treatment with radiation. The amount of the compound, salt, solvate or prodrug in this method can be determined according to the means for ascertaining effective amounts of such compounds described herein.

This invention also relates to a method of and to a pharmaceutical composition for inhibiting abnormal cell growth in a mammal which comprises an amount of a compound of formula 1 or 2, or prodrug thereof, pharmaceutically acceptable salt or solvate of said compound and said prodrug, or an isotopically-labelled derivative thereof, and an amount of one or more substances selected from anti-angiogenesis agents, signal transduction inhibitors, and antiproliferative agents.

Anti-angiogenesis agents, such as MMP-2 (matrix-metalloproteinase 2) inhibitors, MMP-9 (matrix-metalloprotienase 9) inhibitors, and COX-II (cyclooxygenase II) inhibitors, can be used in conjunction with a compound of formula 1 or 2 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are Prinomastat (AG-3340), RO 32-3555, RS 13-0830, and the compounds recited in the following list
3-[[4-(4-fluoro-phenoxy)-benzenesulfonyl]-(1-hydroxycarbamoyl-cyclopentyl)-amino]-propionic acid;
3-exo-3-[4-(4-fluoro-phenoxy)-benzenesulfonylamino]-8-oxa-bicyclo[3.2.1]octane-3-carboxylic acid hydroxyamide;
(2R,3R)1-[4-(2-chloro-4-fluoro-benzyloxy)-benzenesulfonyl]-3-hydroxy-3-methyl-piperidine-2-carboxylic acid hydroxyamide;
4-[4-(4-fluoro-phenoxy)-benzenesulfonylamino]-tetrahydro-pyran-4-carboxylic acid hydroxyamide;
3-[[4-(4-fluoro-phenoxy)-benzenesulfonyl]-(1-hydroxycarbamoyl-cyclobutyl)-amino]-propionic acid;
4-[4-(4-chloro-phenoxy)-benzenesulfonylamino]-tetrahydro-pyran-4-carboxylic acid hydroxyamide;
(R)3-[4-(4-chloro-phenoxy)-benzenesulfonylamino]-tetrahydro-pyran-3-carboxylic acid hydroxyamide;
(2R,3R)1-[4-(4-fluoro-2-methyl-benzyloxy)-benzenesulfonyl]-3-hydroxy-3-methyl-piperidine-2-carboxylic acid hydroxyamide;
3-[[4-(4-fluoro-phenoxy)-benzenesulfonyl]-(1-hydroxycarbamoyl-1-methyl-ethyl)-amino]-propionic acid;
3-[[4-(4-fluoro-phenoxy)-benzenesulfonyl]-(4-hydroxycarbamoyl-tetrahydro-pyran-4-yl)-amino]-propionic acid;
3-exo-3-[4-(4-chloro-phenoxy)-benzenesulfonylamino]-8-oxa-bicyclo[3.2.1]octane-3-carboxylic acid hydroxyamide;
3-endo-3-[4-(4-fluoro-phenoxy)-benzenesulfonylamino]-8-oxa-bicyclo[3.2.1]octane-3-carboxylic acid hydroxyamide; and
(R) 3-[4-(4-fluoro-phenoxy)-benzenesulfonylamino]-tetrahydro-furan-3-carboxylic acid hydroxyamide;
and pharmaceutically acceptable salts and solvates of said compounds.

Other anti-angiogenesis agents, including other COX-II inhibitors and other MMP inhibitors, can also be used in the present invention.

A compound of formula 1 or 2, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9,1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compounds of the present invention.

The compounds of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The subject invention also includes isotopically-labelled compounds, which are identical to those recited in formula 1 or 2, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased In vivo half-life or reduced dosage requirements and, hence, may be preferred in some circumstances. Isotopically labelled compounds of formula 1 or 2 of this invention and prodrugs thereof can generally be prepared by carrying out the procedures disclosed in the Schemes and/or in the Examples below, by substituting a readily available isotopically labelled reagent for a non-isotopically labelled reagent.

The compounds of formula 1 or 2 and their pharmaceutically acceptable salts and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals having straight, cyclic or branched moieties. Said "alkyl" group may include an optional carbon-carbon double or triple bond where said alkyl group comprises at least two carbon atoms. It is understood that for cyclic moieties at least three carbon atoms are required in said alkyl group.

The term "alkoxy", as used herein, unless otherwise indicated, means O-alkyl groups wherein "alkyl" is as defined above.

The term "aryl", as used herein, unless otherwise indicated, means an organic radical derived from an aromatic hydrocarbon by removal of one hydrogen, such as phenyl or naphthyl.

The terms "5 membered heterocyclic", "5 or 6 membered heterocyclic", "5 to 8 membered heterocyclic", "5 to 10 membered heterocyclic" or "5 to 13 membered heterocyclic", as used herein, unless otherwise indicated, includes aromatic and non-aromatic heterocyclic groups containing one to four heteroatoms each selected from O, S and N, wherein each heterocyclic group has from 5, 6, 5 to 8, 5 to 10 or 5 to 13 atoms in its ring system. The heterocyclic groups include benzo-fused ring systems and ring systems substituted with one or two oxo (=O) moieties such as pyrrolidin-2-one. An example of a 5 membered heterocyclic group is thiazolyl, an example of a 10 membered heterocyclic group is quinolinyl, and an example of a 13 membered heterocyclic group is a carbazole group. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl, benzofuranyl, and benzo[1,3]dioxolyl.

The phrase "pharmaceutically acceptable salt(s)", as used herein, unless otherwise indicated, means salts of acidic or basic groups which may be present in the compounds or prodrugs of formulas 1 and 2. The compounds and prodrugs of formulas 1 and 2 that are basic in nature are capable of forming a wide variety of salts with various inorganic and organic acids. The acids that may be used to prepare pharmaceutically acceptable acid addition salts of such basic compounds and prodrugs of formulas 1 and 2 are those that form non-toxic acid addition salts, i.e. salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentsinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds and prodrugs of the formulas 1 and 2 that are acidic in nature, are capable of forming base salts with various pharmacologically acceptable cations. Examples of such salts include the alkali metal or alkaline earth metal salts and particularly, the sodium and potassium salts.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of present invention may in certain instances exist as tautomers. This invention relates to the use of all such tautomers and mixtures thereof.

The term "prodrug", as used herein, unless otherwise indicated, means compounds that are drug precursors, which following administration, release the drug in vivo via some chemical or physiological process (e.g., a prodrug on being brought to the physiological pH is converted to the desired drug form).

Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formulas 1 and 2. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

It will be appreciated that any solvate (e.g. hydrate) form of compounds of formulas 1 and 2 and prodrugs thereof can be used for the purpose of the present invention.

DETAILED DESCRIPTION OF THE INVENTION

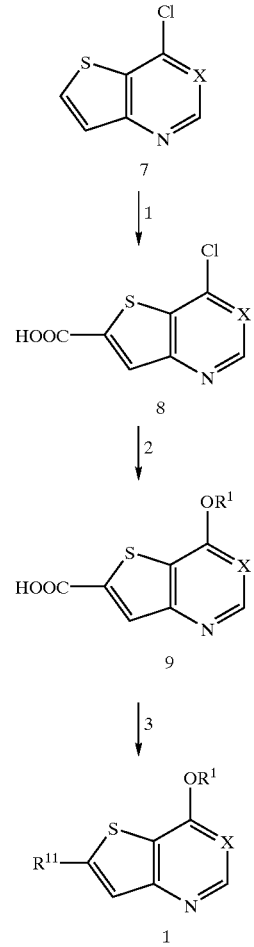

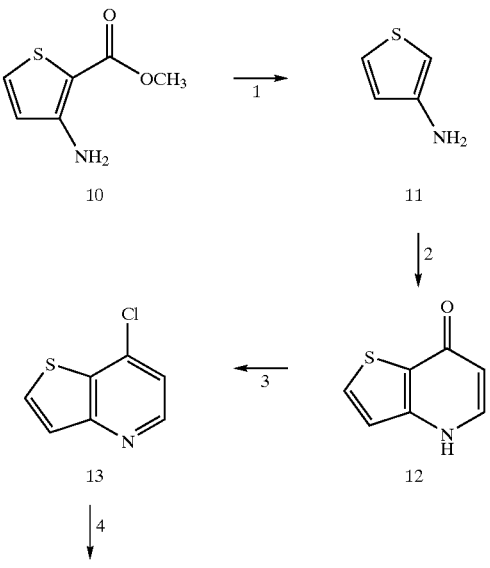

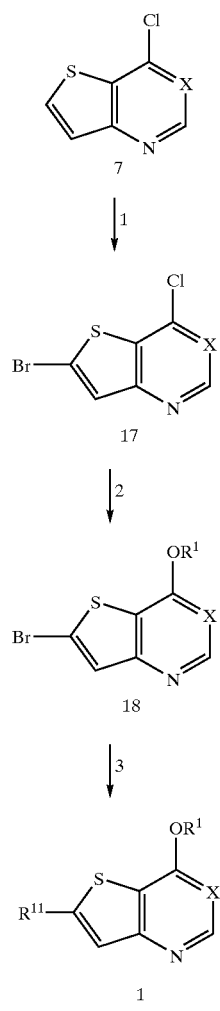
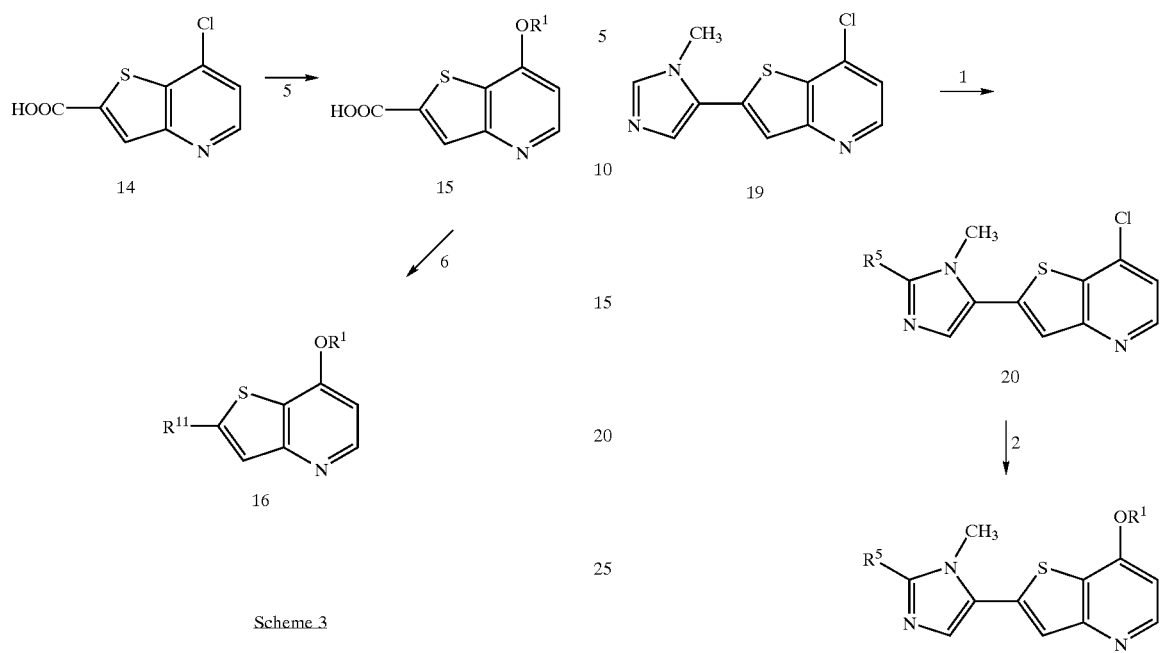
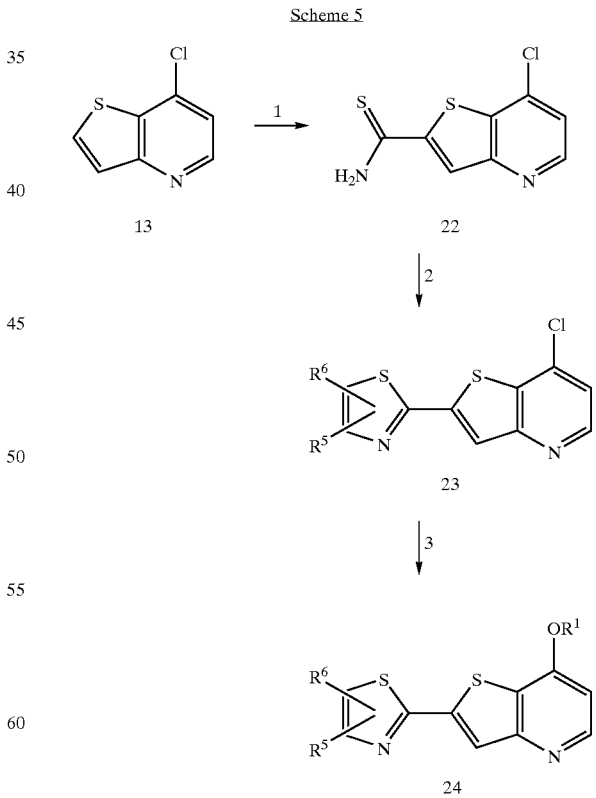
The compounds of the present invention are prepared using the following thienopyridine and thienopyrimidine synthetic intermediates:

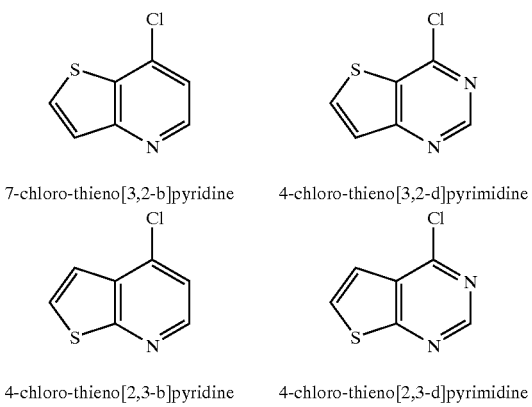

7-chloro-thieno[3,2-b]pyridine    4-chloro-thieno[3,2-d]pyrimidine 4-chloro-thieno[2,3-b]pyridine    4-chloro-thieno[2,3-d]pyrimidine The examples of the present invention employ the 7-chloro-thieno[3,2-b]-pyridine as a synthetic intermediate. Methods to prepare the following regiosiomers, 4-chloro-thieno[2,3-b]pyridine, 4-chloro-thieno[3,2-d]pyrimidine and 4-chloro-thieno[2,3-d]pyrimidine as synthetic intermediates are well known to those skilled in the art. For example, the regioisomer 4-chloro-thieno[2,3-b]pyridine may be prepared in the manner described in Klemm, L. H.; Hartling, R.; J. Heterocycl. Chem. 1976 13(6), pages 1197–1200, which is hereby incorporated in its entirety by reference. The syntheses of regiosiomers 4-chloro-thieno[3,2-d]pyrimidine and 4-chloro-thieno[2,3-d]pyrimidine are described in U.S. Pat. No. 5,654,307, which is hereby incorporated in its entirety by reference. Accordingly, the synthetic intermediate 7-chloro-thieno[3,2-b]-pyridine employed in the examples and schemes of the present invention can be readily substituted by any of the regioisomeric synthetic intermediates, 4-chloro-thieno[2,3-b]pyridine, 4-chloro-thieno[3,2-d]pyrimidine and 4-chloro-thieno[2,3-d]pyrimidine.

The preparation of the compounds of the present invention is illustrated in Schemes 1–5 and described below.

The compounds of the present invention are readily prepared according to synthetic methods familiar to those skilled in the art. Scheme 1 illustrates a general synthetic procedure for preparing the compounds of the present invention. The compound of formula 7, in which X is CH or N, may be prepared by one or more procedures described in published PCT international applications numbers WO 95/19774 (published Jul. 27, 1995), WO 95/19970 (published Jul. 27, 1995), and WO 97/13771 (published Apr. 17, 1997). In addition, 4-chlorothieno[3,2-d]pyrimidine is commercially available from Maybridge Chemical Co. Ltd, Cornwall, England. A preferred method of preparing 4-chlorothieno[3,2-d]pyridine is described below with reference to steps 1–3 of Scheme 2.

In step 1 of Scheme 1, the compound of formula 7 may be converted to the corresponding carboxy derivative of formula 8 by treating the starting compound, for example, with lithium diisopropylamine or n-butyllithium, and then carbon dioxide gas in a non-polar solvent, such as tetrahydrofuran (THF), at a temperature of about −78° C. for a period of about 15 minutes to one-half hour and then gradually warming the mixture to room temperature (20–25° C).

In step 2 of Scheme 1, the compound of formula 8 may be coupled with a compound of formula HOR$^1$, wherein R$^1$ is as defined above, optionally in the presence of a base, such as cesium carbonate, pyridine, triethylamine or sodium hydride, under an inert atmosphere, such as dry nitrogen gas, in a solvent, such as a C$_1$–C$_6$ alcohol, dimethylformamide (DMF), 1,2-dichloroethane (DCE), N-methylpyrrolidin-2-one (NMP), chloroform, acetonitrile, tetrahydrofuran (THF), dimethylsulfoxide (DMSO), 1,4-dioxane or pyridine, or a mixture of two or more of the foregoing solvents, preferably a mixture of t-butyl alcohol and DCE, at a temperature of from ambient to reflux temperature, preferably 80–125° C., for a period of about 2 hours to 72 hours to provide the compound of formula 9.

Where the compound of formula HOR$^1$ is an optionally substituted indole or indoline moiety, such compounds can be prepared according to one or more methods known to those skilled in the art. Such methods are described in PCT international patent application publication number WO 95/23141, referred to above, and in W. C. Sumpter and F. M. Miller, "Heterocyclic Compounds with Indole and Carbazole Systems," in volume 8 of "The Chemistry of Heterocyclic Compounds", Interscience Publishers Inc., New York (1954). Where the compound of formula HOR$^1$ is an optionally substituted quinoline, isoquinoline, or quinazoline derivative, such compounds can also be prepared according to one or more methods known to those skilled in the art. Such methods are described in A. R. Katrizky, C. W. Rees, and E. F. V. Scriven, "Comprehensive Heterocyclic Chemistry II", volumes 5, 6, and 7, Elsevier Science Ltd., Oxford (1996). Optional substituents can be included as appropriate before or after the coupling step illustrated in Scheme 1. Prior to the coupling step, hydroxy and primary and secondary amino moieties (other than said hydroxy of formula HOR$^1$) are preferably protected using a nitrogen protecting group known to those skilled in the art. Such protecting groups and their use are described in T. W. Greene and P. G. M. Wuts, "Protective Groups in Organic Synthesis," Second Edition, John Wiley & Sons, New York, 1991.

In step 3 of Scheme 1, transformation of the carboxy derivative of formula 9 to the compound of formula 1 is carried out using standard synthetic methods well known to those of ordinary skill in the art, such as described in B. S. Furniss, A. J. Hannaford, P. W. G. Smith and A. R. Tatchell, "Vogel's Textbook of Practical Organic Chemistry," Fifth Edition, Longman, Harlow, England, 1996. Optional substituents on the R$^{11}$ group can be included as appropriate using methods well known to those of ordinary skill in the art, before or after step 3 of Scheme 1.

In the alternative, steps 2 and 3 of Scheme 1 may be reversed. That is, the R$^{11}$ group may be introduced into the compound of formula prior to the addition of HOR$^1$ as described above.

Scheme 2 illustrates a procedure for preparing the compounds of formula 16 wherein X is CH. In step 1 of Scheme 2, the compound of formula 10 (3-amino-thiophene-2-carboxylic acid methyl ester) is dissolved in sodium hydroxide and refluxed for about 2 hours. The solution is then cooled to 0° C. and acidified to pH 5 with concentrated HCl at which time a precipitate will form. The precipitate is separated and treated with propanol and oxalic acid, and the solution is stirred at about 38° C. for approximately 45 minutes to provide the compound of formula 11 (thiophen-3-ylamine). In step 2 of Scheme 2, the compound of formula 11 is dissolved in triethyl orthoformate and stirred at room temperature until dissolution is complete. 2,2-Dimethyl-[1,3]dioxane-4,6-dione is then added portionwise at room temperature, with a precipitate forming upon completion of the addition. The mixture is then heated at 85° C. overnight. The resulting precipitate, (2,2-dimethyl-5-(thiophen-3- ylaminomethylene)-[1,3]dioxane-4,6-dione), is then separated and washed. The intermediate is added to dowtherm A (heated to 260° C.), and the resulting mixture is heated for 30 minutes and then cooled to room temperature to provide the compound of formula 12. In step 3 of Scheme 2, the compound of formula 12 is added to oxalyl chloride in a mixture of methylene chloride and DMF and heated to reflux for approximately two hours to provide the compound of formula 13. The compound of formula 13 may be converted to the compound of formula 14 as described above with respect to step 1 of Scheme 1. The compound of formula 14 may be converted to the compound of formula 15 as described above with respect to step 2 of Scheme 1. The compound of formula 15 may be converted to the compound of formula 16 as described above with respect to step 3 of Scheme 1.

In order to make a compound of formula 1 wherein $R^{11}$ is —C(O)$NR^{12}R^{13}$, the compound of formula 15 is coupled, for example, with $HNR^{12}R^{13}$ using coupling methods well known to those of ordinary skill in the art and found, for example, in PCT international application number WO 94/07910, which is incorporated herein by reference in its entirety. Alternatively, the compound of formula 14 can be transformed into the acid chloride derivative by treating it with oxalyl or thionyl chloride in dichloromethane at room temperature for 2–4 hours. The resulting acid chloride is then treated with a compound of formula $HNR^{12}R^{13}$ to provide the desired compound of formula 1 wherein $R^{11}$ is an amide derivative.

A compound of formula 1 wherein $R^{11}$ is a sulfonyl derivative can be prepared by treating a compound of formula 7 as described in step 1 of Scheme 1, with sulfonyl or sulfonamidyl halide in place of carbon dioxide.

When the $R^{11}$ substituent of formula 1 is linked through an amino group, transformation of the carboxy group of compound 8 to the amino group is first required. This can be accomplished using the Curtius reaction, wherein the acid chloride derivative of compound 8 is treated with, for example, sodium azide, and the resulting acyl azide is allowed to decompose in the presence of acid to afford the amino derivative. The resulting amino compound can be further functionalized by acylating with a variety of carboxylic acids, acid chlorides, sulfonic acids, sulfonyl chlorides, or guanylating agents to produce a variety of $R^{11}$ groups, such as, —$NR^{12}C(=O)R^{13}$, —$NR^9SO_2R^{12}$, —$NR^9SO_2NR^{12}R^{13}$, —$NR^9C(=NR^{12})R^{13}$, and—$NR^9C(=NR^{12})NR^9R^{13}$.

Scheme 3 illustrates a second general synthetic procedure for preparing the compounds of the present invention. In step 1 of Scheme 3, the compound of formula 7 may be converted to the corresponding bromo derivative of formula 17 by treating the starting compound with lithium diisopropylamine or n-butyllithium, and then 1,2-dibromo-1,1,2,2-tetrafluoroethane or bromine in a non-polar solvent, such as tetrahydrofuran CRHF), at a temperature of about −78° C. for a period of about 15 minutes to one-half hour and then gradually warming the mixture to room temperature (20–25° C.).

In step 2 of Scheme 3, the compound of formula 17 may be coupled with a compound of formula $HOR^1$, wherein $R^1$ is as defined above, optionally in the presence of a base, such as cesium carbonate, pyridine, triethylamine or sodium hydride, under an inert atmosphere, such as dry nitrogen gas, in a solvent, such as t-butyl alcohol, dimethylformamide (DMF), 1,2-dichloroethane (DCE), N-methylpyrrolidin-2-one (NMP), chloroform, acetonitrile, tetrahydrofuran (THF), dimethylsulfoxide (DMSO), 1,4-dioxane or pyridine, or a mixture of two or more of the foregoing solvents, preferably a mixture of t-butyl alcohol and DCE, at a temperature of from ambient to reflux temperature, preferably 80–125° C., for a period of about 2 hours to 72 hours to provide the compound of formula 18. The foregoing reaction is preferably done in a sealed tube.

In step 3 of Scheme 3, the compound of formula 18 may be converted to the compound of formula 1 by coupling the starting compound with a compound of the formula $R_{11}$—B(OH)$_2$ (wherein $R^{11}$ is as defined above) in the presence of 1,4-bis(diphenylphosphino)butane and a palladium catalyst, such as bis(benzonitrile)-palladium(II) chloride, a base, such as sodium or potassium carbonate, and a solvent, such as toluene, ethanol, THF, DMF, or dimethoxyethane (DME), preferably a mixture of toluene, ethanol and THF, at a temperature within the range of about 50–110° C. for a period of about 1 to 24 hours. This step is analogous to the Suzuki coupling procedure described in N. Miyaura, A. Suzuki, *Chem. Rev.* 1995, 95, 2457.

In the alternative, steps 2 and 3 of Scheme 3 may be reversed. That is, the $R^{11}$ group may be introduced into the compound of formula 7 followed by the coupling of the resulting compound with the compound of formula $HOR^1$ as described above.

In another procedure, step 3 of Scheme 3 may be achieved by reacting the compound of formula 18 with a compound of the formula (trialkylstannyl)-$R^{11}$ (wherein $R^{11}$ is as defined above), such as (tributylstannyl)-$R^{11}$, in the presence of copper iodide and trans-benzyl(chloro)bis(triphenylphosphine)palladium(II) in DMF at a temperature of about 90° C. for a period of about 14 hours. The starting compound for this procedure, specifically (tributylstannyl)-$R^{11}$, may be prepared from $R^{11}$—Br by at least three separate procedures. In a first procedure, $R^{11}$—Br may be treated with (tributylstannyl)-chloride and n-butyllithium in THF or DMF to provide (tributylstannyl)-$R^{11}$. In a second procedure, $R^{11}$—Br may be treated with $Bu_3Sn$—$SnBu_3$, wherein Bu represents butyl, and sodium metal to provide (tributylstannyl)-$R^{11}$. And in a third procedure, $R^{11}$—Br may be treated with $Bu_3Sn$—$SnBu_3$, wherein Bu represents butyl, and Pd(PPh$_3$)$_4$, wherein Ph represents phenyl, in toluene to provide (tributylstannyl)-$R^{11}$.

Following or before step 3 of Scheme 3, the $R^{11}$ group may be modified to introduce one or more $R^5$ groups (wherein $R^5$ is as defined above). In a one preferred method, where $R^{11}$ is a heteroaryl group that includes an aldehyde group, the aldehyde may be converted to a preferred aminomethyl group. In this process, the starting compound that includes an aldehyde on the $R^{11}$ group is reacted with an amine of the formula $HNR^6R^7$ (wherein $R^6$ and $R^7$ are as defined above) in the presence of a reducing agent, such as sodium cyanoborohydride or sodium borohydride, in a solvent comprising acetic acid and ethanol or methanol at a temperature in the range of 0–100° C., preferably room temperature. This process converts the aldehyde to a moiety of the formula $R^6R^7NCH_2$—.") Other methods of modifying the compounds of formula 1 will be obvious to those skilled in the art.

Scheme 4 illustrates a procedure for preparing the compounds of formula 1 wherein X is CH and $R^{11}$ is substituted imidiazole. The compound of formula 19 is prepared as described in WO 99/2440, hereby incorporated by reference.

Scheme 5 illustrates a procedure for preparing the compounds of formula 1 wherein X is CH and $R^{11}$ is substituted thiazole. The preparation of the compound of formula 22 is described in Example 16. Thiazole compounds of formula 23 can be prepared by combining compound 22 with alphahalo aldehydes or ketones under the conditions described in A. R. Katrizky and C. W. Rees, "Comprehensive Heterocyclic Chemistry", volume 6, chapter 4.19, Pergamon Press, Oxford (1984). Optional substituents can be included as appropriate before or after the introduction of the introduction of the compound HOR$^1$ in step 3 of Scheme 5.

The compounds of formulas 1 and 2 that are basic in nature are capable of forming a wide variety of different salts with various inorganic and organic acids. Although such salts must be pharmaceutically acceptable for administration to animals, it is often desirable in practice to initially isolate the compound of formula 1 or 2 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formulas 1 and 2 that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulas 1 and 2. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention are potent inhibitors of the erbB family of oncogenic and protooncogenic protein tyrosine kinases such as epidermal growth factor receptor (EGFR), erbB2, HER3, or HER4 and thus are all adapted to therapeutic use as anti-proliferative agents (e.g., anticancer) in mammals, particularly in humans. The compounds of the present invention are also inhibitors of angiogenesis and/or vasculogenesis. In particular, the compounds of the present invention are useful in the prevention and treatment of a variety of human hyperproliferative disorders such as malignant and benign tumors of the liver, kidney, bladder, breast, gastric, ovarian, colorectal, prostate, pancreatic, lung, vulval, thyroid, hepatic carcinomas, sarcomas, glioblastomas, head and neck, and other hyperplastic conditions such as benign hyperplasia of the skin (e.g., psoriasis) and benign hyperplasia of the prostate (e.g., BPH). It is, in addition, expected that a compound of the present invention may possess activity against a range of leukemias and lymphoid malignancies.

The compounds of the present invention may also be useful in the treatment of additional disorders in which aberrant expression ligand/receptor interactions or activation or signalling events related to various protein tyrosine kinases, are involved. Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases are involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the compounds of formulas 1 and 2 in inhibiting the receptor tyrosine kinase (and thus subsequent proliferative response, e.g., cancer) may be determined by the following procedure.

The activity of the compounds of formulas 1 and 2, in vitro, can be determined by the amount of inhibition of the phosphorylation of an exogenous substrate (e.g., Lys$_3$-Gastrin or polyGluTyr (4:1) random copolymer (I. Posner et al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, *Methods in Enzymology* 146, 82–88 (1987) from A431 cells (American Type Culture Collection, Rockville, Md.) and preincubated in a microfuge tube with EGF (2 µg/ml) in phosphorylation buffer+vanadate (PBV: 50 mM HEPES, pH 7.4; 125 mM NaCl; 24 mM MgCl$_2$; 100 µM sodium orthovanadate), in a total volume of 10 µl, for 20–30 minutes at room temperature. The test compound, dissolved in dimethylsulfoxide (DMSO), is diluted in PBV, and 10 µl is mixed with the EGF receptor /EGF mix, and incubated for 10–30 minutes at 30° C. The phosphorylation reaction is initiated by addition of 20 µl $^{33}$P-ATP/substrate mix (120 µM Lys$_3$-Gastrin (sequence in single letter code for amino acids, KKKGPWLEEEEEAYGWLDF), 50 mM Hepes pH 7.4, 40 µM ATP, 2 µCi γ-[$^{33}$P]-ATP) to the EGFr/EGF mix and incubated for 20 minutes at room temperature. The reaction is stopped by addition of 10 µl stop solution (0.5 M EDTA, pH 8; 2 mM ATP) and 6 µl 2N HCl. The tubes are centrifuged at 14,000 RPM, 4° C., for 10 minutes. 35 µl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., lys$_3$-gastrin) is subtracted from all values as a background and percent inhibition is calculated relative to controls without test compound present. Such assays, carried out with a range of doses of test compounds, allow the determination of an approximate IC$_{50}$ value for the in vitro inhibition of EGFR kinase activity.

The activity of the compounds of formulas 1 and 2, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.,*

35, 2434–2439 (1975) and Corbett, T. H., et al., "A Mouse Colon-tumor Model for Experimental Therapy", *Cancer Chemother. Rep. (Part 2)*", 5 , 169–186 (1975), with slight modifications. Tumors are induced in the left flank by s.c. injection of 1×10$^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic™ P105 in 0.9% saline) by the intraperitoneal (ip) or oral (po) routes of administration twice daily , every 12 hours) for 5 consecutive days. In order to determine an anti-tumor effect, the tumor is measured in millimeters with Vernier calipers across two diameters and the tumor size (mg) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). Results are expressed as percent inhibition, according to the formula: Inhibition (%)= (TuW$_{control}$−TuW$_{test}$)/TuW$_{control}$×100%. The flank site of tumor implantation provides reproducible dose/response effects for a variety of chemotherapeutic agents, and the method of measurement (tumor diameter) is a reliable method for assessing tumor growth rates.

Other methods of assessing the activity of the compounds of the present invention are referred to in PCT international application publication number WO 95/21613 (published Aug. 17, 1995) which incorporated herein by reference.

The in vitro activity of the compounds of formulas 1 and 2 in inhibiting the KDR/VEGF receptor may be determined by the following procedure.

The ability of the compounds of the present invention to inhibit tyrosine kinase activity may be measured using a recombinant enzyme in an assay that measures the ability of compounds to inhibit the phosphorylation of the exogenous substrate, polyGluTyr (PGT, Sigma™, 4:1). The kinase domain of the human KDR/VEGF receptor (amino acids 805–1350) is expressed in Sf9 insect cells as a glutathione S-transferase (GST)-fusion protein using the baculovirus expression system. The protein is purified from the lysates of these cells using glutathione agarose affinity columns. The enzyme assay is performed in 96-well plates that are coated with the PGT substrate (0.625 µg PGT per well). Test compounds are diluted in dimethylsulfoxide (DMSO), and then added to the PGT plates so that the final concentration of DMSO in the assay is 1.6% (v/v). The recombinant enzyme is diluted in phosphorylation buffer (50 mM Hepes, pH 7.3, 125 mM NaCl, 24 mM MgCl$_2$). The reaction is initiated by the addition of ATP to a final concentration of 10 µM. After a 30 minute incubation at room temperature with shaking, the reaction is aspirated, and the plates are washed with wash buffer (PBS-containing 0.1% Tween-20). The amount of phosphorylated PGT is quantitated by incubation with a HRP-conjugated (HRP is horseradish peroxidase) PY-54 antibody (Transduction Labs), developed with TMB peroxidase (TMB is 3,3',5,5'-tetramethylbenzidine), and the reaction is quantitated on a BioRad™ Microplate reader at 450 nM. Inhibition of the kinase enzymatic activity by the test compound is detected as a reduced absorbance, and the concentration of the compound that is required to inhibit the signal by 50% is reported as the IC$_{50}$ value for the test compound.

To measure the ability of the compounds to inhibit KDR tyrosine kinase activity for the full length protein that exists in a cellular context, the porcine aortic endothelial (PAE) cells transfected with the human KDR (Waltenberger et al., J. Biol. Chem. 269:26988, 1994) may be used. Cells are plated and allowed to attach to 96-well dishes in the same media (Ham's F12) with 10% FBS (fetal bovine serum). The cells are then washed, re-fed with serum depleted media that contains 0.1% (v/v) bovine serum albumin (BSA), and allowed to incubate for 24 hours. Immediately prior to dosing with compound, the cells are re-fed with the serum depleted media (without BSA). Test compounds, dissolved in DMSO, are diluted into the media (final DMSO concentration 0.5% (v/v)). At the end of a 2 hour incubation, VEGF$_{165}$ (50 ng/ml final) is added to the media for an 8 minute incubation. The cells are washed and lysed in HNTG buffer (20 mM Hepes, pH 7.5, 150 mM NaCl, 0.2% Triton™ X-100, 10% glycerol, 0.2 mM PMSF (phenylmethylsulfonyl fluoride), 1 µg/ml pepstatin, 1 µg/ml leupeptin, 1 µg/ml aprotonin, 2 mM sodium pyrophosphate, 2 mM sodium orthovanadate). The extent of phosphorylation of KDR is measured using an ELISA assay. The 96-well plates are coated with 1 µg per well of goat anti-rabbit antibody. Unbound antibody is washed off the plate and remaining sites are blocked with Superblock buffer (Pierce) prior to addition of the anti-flk-1 C-20 antibody (0.5 µg per plate, Santa Cruz). Any unbound antibody is washed off the plates prior to addition of the cell lysate. After a 2 hour incubation of the lysates with the flk-1 antibody, the KDR associated phosphotyrosine is quantitated by development with the HRP-conjugated PY-54 antibody and TMB, as described above. The ability of the compounds to inhibit the VEGF-stimulated autophosphorylation reaction by 50%, relative to VEGF-stimulated controls is reported as the IC$_{50}$ value for the test compound.

The ability of the compounds to inhibit mitogenesis in human endothelial cells is measured by their ability to inhibit $^3$H-thymidine incorporation into HUVE cells (human umbilical vein endothelial cells, Clonetics™). This assay has been well described in the literature (Waltenberger J et al. J. Biol. Chem. 269: 26988, 1994; Cao Y et al. J. Biol. Chem. 271: 3154, 1996). Briefly, 10$^4$ cells are plated in collagen-coated 24-well plates and allowed to attach. Cells are re-fed in serum-free media, and 24 hours later are treated with various concentrations of compound (prepared in DMSO, final concentration of DMSO in the assay is 0.2% v/v), and 2–30 µg/ml VEGF$_{165}$. During the last 3 hours of the 24 hour compound treatment, the cells are pulsed with $^3$H thymidine (NEN, 1 µCi per well). The media are then removed, and the cells washed extensively with ice-cold Hank's balanced salt solution, and then 2 times with ice cold trichloroacetic acid (10% v/v). The cells are lysed by the addition of 0.2 ml of 0.1 N NaOH, and the lysates transferred into scintillation vials. The wells are then washed with 0.2 ml of 0.1 N HCl, and this wash is then transferred to the vials. The extent of $^3$H thymidine incorporation is measured by scintillation counting. The ability of the compounds to inhibit incorporation by 50%, relative to control (VEGF treatment with DMSO vehicle only) is reported as the IC$_{50}$ value for the test compound.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred antimetabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trfluoromethyl) propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations. As used herein, "h" means hour(s), "min" means minutes, "Et" means ethyl, "THF" means tetrahydrofuran, "DMF" means dimethylformamide, "Ad" means acetyl and "Me" means methyl.

EXAMPLE 1

(3R)-(3-Methoxy-pyrrolidin-1-yl)[-7-(2-methyl-1H-indol-5-yloxy)-thieno[3,2-b]pyridin-2-yl]-methanone A. 7-Chloro-thieno[3,2-b]pyridine The title compound was prepared by the method described in patent WO-99/24440, Example 47, the contents of which are hereby incorporated by reference.

B. Lithium 7-chloro-thieno[3,2-b]pyridine-2-carboxalate n-Butyllithium (0.13 mol, 52 mL of a 2.5M solution in hexane) was added dropwise to a solution of 7-chloro-thieno [3,2-b]pyridine (20 g, 0.12 mol) in THF (200 mL) at −78° C., and the internal temperature was maintained below −70° C. After 1 h the yellow solution was treated with $CO_2(g)$ until a white suspension resulted. The resulting mixture was allowed to warm to room temperature, then concentrated under reduced pressure to give a white solid. The resulting solid was triturated with ether then dried in vacuo to afford the title compound as a white solid (23.5 g, 90%). MS: 213 (MH+); HPLC Rf: 2.50 min.; HPLC purity. 94%.

C. (3R)-(3-hydroxy-pyrrolidin-1-yl)-[7-chloro-thieno[3,2-b]pyridin-2-yl]-methanone A solution of lithium 7-chloro-thieno[3,2-b]pyridine-2-carboxylate (15.0 g, 70.8 mmol), thionyl chloride (53.1 mL, 106.2 mmol), $CH_2Cl_2$ (600 ml), and DMF (6 ml) was heated to reflux. After 3 h the resulting yellow solution was concentrated under reduced pressure, and the residue was suspended in $CH_2Cl_2$ (500 mL). (3R)-pyrrolidin-3-ol (2.3 g, 26.2 mmol) was then added dropwise. After 12 h the reaction was quenched with 1N NaOH (500 mL), the layers were separated, and the aqueous layer was extracted with 2×500 mL $CH_2Cl_2$. The combined organic layers were dried over $Na_2SO_4$, filtered, then concentrated under reduced pressure. The resulting solid was triturated with $Et_2O$ then collected by filtration to give a white solid (13.2 g, 70%). MS: 283.2/285.2 (MH+); HPLC Rf: 3.49 min.; HPLC purity: 99%.

D. (3R)-(7-Chloro-thieno[3,2-b]pyridin-2-yl)-(3-methoxy-pyrrolidin-1-yl)-methanone NaH (2.1 g, 53.1 mmol) was added to a solution of (3R)-(3-hydroxy-pyrrolidin-1-yl)-[7-chloro-thieno[3,2-b]pyridin-2-yl]-methanone (5.0 g, 17.7 mmol) in THF (100 mL), at 0° C. The reaction mixture was allowed to stir for 20 min., and MeI (3.26 g, 22.9 mmol) was added dropwise. After 3 h the reaction was treated with saturated aqueous KCN. The aqueous layer was extracted with CH$_2$Cl$_2$. The combined organic layers were dried (Na$_2$SO$_4$), and the solvent was removed under reduced pressure. Purification by flash chromatography on silica gel, eluting with CH$_2$Cl$_2$/MeOH (94:6) afforded the title compound as a white solid (3.2 g, 61%). MS: 297.2/299.2 (MH+); HPLC Rf: 4.25 min.; HPLC purity: 95%.

E. 2-Methyl-1H-indol-5-ol

To a solution of 5-methoxy-2-methyl-1H-indole (5 g, 31 mmol) in methylene chloride (100 mL) at −78° C., was slowly added a solution of BBr$_3$ in CH$_2$Cl$_2$ (1.0 M, 93 mL, 93 mmol). The reaction mixture was stirred at −78° C. for 4 hours and slowly warmed to room temperature. The reaction mixture was stirred at room temperature overnight, and cooled to 0° C. The reaction was quenched carefully with water at 0° C. The aqueous layer was made basic by adding saturated sodium bicarbonate solution, and then extracted with methylene chloride (3×50 mL). The combined organic layers were dried over sodium sulfate and concentrated under reduced pressure. The crude product was purified by flash chromatography on silica gel eluting with EtOAc/Hexanes (25:75) to afford the title compound as a yellow solid (3.0 g, 60%).

F. (3R)-(3-Methoxy-pyrrolidin-1-yl)-[7-(2-methyl-1H-indol-5-yloxy)-thieno[3,2-b]pyridin-2-yl]-methanone Cs$_2$CO$_3$ (0.495 g, 1.52 mmol) was added to a solution of (3R)-(7-chloro-thieno[3,2-b]pyridin-2-yl)-(3-methoxy-pyrrolidin-1-yl)-methanone (0.228 g, 0.76 mmol) and 2-methyl-1H-indol-5-ol (0.223 9, 1.52 mmol) in DMF (5 mL), and the resulting solution was heated to 90° C. After 20 h the reaction was quenched with water, EtOAc was added, and the layers were separated. The aqueous layer was extracted with EtOAc, and the combined organic layers were dried over Na$_2$SO$_4$ then concentrated. The resulting material was purified on silica gel by flash column chromatography, eluting with CH$_2$Cl$_2$/MeOH (98/2) to afford the title compound as a white solid (0.26 g, 84%). MS: 408.8 (MH+); HPLC Rf: 5.394 min.; HPLC purity: 97%.

EXAMPLE 2

(3S)-(3-Methoxy-pyrrolidin-1-yl)-[7-(2-methyl-1H-indol-5-yloxy)-thieno[3,2-b]pyridin-2-yl]-methanone The title compound was prepared from (3S)-pyrrolidin-3-ol as starting material, by a procedure analogous to Example 1. MS: 408.5 (MH+); HPLC Rf: 5.41 min.; HPLC purity: 98%.

EXAMPLE 3

(3R,4R)-(3,4-Dimethoxy-pyrrolidin-1-yl)-[7-(2-methyl-1H-indol-5-yloxy)-thieno[3,2-b]pyridin-2-yl]-methanone A. (3R,4R)-(7-Chloro-thieno[3,2-b]pyridin-2-yl)-(3,4-dihydroxy-pyrrolidin-1-yl)-methanone The title compound was prepared from lithium 7-chloro-thieno[3,2-b]pyridine-2-carboxylate and (3R,4R)-pyrrolidine-3,4-diol by a procedure analogous to Example 1C. MS: 299.3/301.3 (MH+); HPLC Rf: 3.091 min.; HPLC purity: 99%.

B. (3R,4R)-(7-Chloro-thieno[3,2-b]pyridin-2-yl)-(3,4-dimethoxy-pyrrolidin-1-yl)-methanone NaH (169 mg, 4.23 mmol) was added to a solution of (3R,4R)-(7-chloro-thieno[3,2-b]pyridin-2-yl)-(3,4-dihydroxy-pyrrolidin-1-yl)-methanone (421 mg, 1.41 mmol) in DMF at 0° C. After 1 h, MeI (500 mg, 3.52 mmol) was added dropwise. The resulting solution was allowed to warm to room temperature and stir for 1.5 h. The reaction mixture was treated with saturated KCN (aq) and saturated ammonium chloride (aq). The aqueous layer was extracted with EtOAc (2×), and the combined organic layers were dried over magnesium sulfate. The resulting material was purified on silica gel by flash column chromatography eluting with CH$_2$Cl$_2$/MeOH (98/2) to afford the title compound as a white solid (324 mg, 70%). MS: 327.2/329.2 (MH+); HPLC Rf: 4.448 min.; HPLC purity: 99%.

C. (3R,4R)-(3,4-Dimethoxy-pyrrolidin-1-yl)-[7-(2-methyl-1H-indol-5-yloxy)-thieno[3,2-b]pyridin-2-yl]-methanone The title compound was prepared from (3R,4R)-(7-chloro-thieno[3,2-b]pyridin-2-yl)-(3,4-dimethoxy-pyrrolidin-1-yl)-methanone and 2-methyl-1H-indol-5-ol by a procedure analogous to Example 1F. MS 438.3 (MH+); HPLC Rf: 5.554 min.; HPLC purity: 97%.

EXAMPLE 4 meso-(3,4-Dimethoxy-pyrrolidin-1-yl)-[7-(2-methyl-1H-indol-5-yloxy)-thieno[3,2-b]pyridin-2-yl]-methanone The title compound was prepared from meso-pyrrolidine-3,4-diol as starting material by a procedure analogous to Example 3. MS: 438.3 (MH+); HPLC Rf: 5.194 min.; HPLC purity: 99%.

EXAMPLE 5

(3S,4S)-(3,4-Dimethoxy-pyrrolidin-1-yl)-[7-(2-methyl-1H-indol-5-yloxy)-thieno[3,2-b]pyridin-2-yl]-methanone The title compound was prepared from (3S,4S)-pyrrolidine-3,4-diol as starting material by a procedure analogous to Example 3. MS: 438.3 (MH+); HPLC Rf: 5.534 min.; HPLC purity 96%.

EXAMPLE 6

(R)-(2-Hydroxymethyl-pyrrolidin-1-yl)-[7-(2-methyl-1H-indol-5-yloxy)-thieno[3,2-b]pyridin-2-yl]-methanone A. (R)-(7-Chloro-thieno[3,2-b]pyridin-2-yl)-(2-hydroxymethyl-pyrrolidin-1-yl)-methanone The title compound was prepared from (R)-pyrrolidin-2-yl-methanol by a procedure analogous to Example 1C. MS: 297.1/299.1 (MH+); HPLC Rf: 3.981 min.; HPLC purity: 97%.

B. (R)-(2-Hydroxymethyl-pyrrolidin-1-yl)-[7-(2-methyl-1H-indol-5-yloxy)-thieno[3,2-b]pyridin-2-yl]-methanone The title compound was prepared from (R)-(7-chloro-thieno[3,2-b]pyridin-2-yl)-(2-hydroxymethyl-pyrrolidin-1-yl)-methanone and 2-methyl-1H-indol-5-ol by a procedure analogous to Example 1F. MS: 408.3 (MH+); HPLC Rf: 5.146 min.; HPLC purity: 98%.

EXAMPLE 7

(S)-(2-Hydroxymethyl-pyrrolidin-1-yl)[-7-(2-methyl-1H-indol-5-yloxy)-thieno[3,2-b]pyridin-2-yl]-methanone The title compound was prepared from (S)-pyrrolidin-2-yl-methanol as starting material by a procedure analogous to Example 6. MS: 408.2 (MH+); HPLC purity: 5.153 min.; HPLC purity: 94%.

EXAMPLE 8

(2R)-(2-Methoxymethyl-pyrrolidin-1-yl)-[7-(2-methyl-1H-indol-5-yloxy)-thieno[3,2-b]pyridin-2-yl]-methanone A. (2R)-(7-Chloro-thieno[3,2-b]pyridin-2-yl)-(2-methoxymethyl-pyrrolidin-1-yl)-methanone The title compound was prepared from lithium 7-chloro-thieno[3,2-b]pyridine-2-carboxylate and 2-methoxymethyl-pyrrolidine by a procedure analogous to Example 1C. MS: 312/314 (MH+); HPLC Rf: 4.87 min; HPLC purity: 99%.

B. (2R)-(2-Methoxymethyl-pyrrolidin-1-yl)-[7-(2-methyl-1H-indol-5-yloxy)-thieno[3,2-b]pyridin-2-yl]-methanone The title compound was prepared from (7-chloro-thieno[3,2-b]pyridin-2-yl)-(2-hydroxymethyl-pyrrolidin-1-yl)-methanone and 2-methyl-1H-indol-5-ol by a procedure analogous to Example 1F. MS: 422 (MH+); HPLC Rf: 5.89 min; HPLC purity: 99%.

EXAMPLE 9

(2S)-(2-Methoxymethyl-pyrrolidin-1-yl)[7-(2-methyl-1H-indol-5-yloxy)-thieno[3,2-b]pyridin-2-yl]-methanone The title compound was prepared by the method described for Example 8, using (2S)-2-methoxymethyl-pyrrolidine as the starting material. MS: 422 (MH+); HPLC Rf: 5.90 min; HPLC purity: 98%.

EXAMPLE 10

(R)-[7-(1-Ethyl-2-methyl-1H-indol-5-yloxy)-thieno[3,2-b]pyridin-2-yl]-(2-methoxymethyl-pyrrolidin-1-yl)-methanone NaH (16 mg, 0.4 mmol) was added to a solution of (2R)-(2-methoxymethyl-pyrrolidin-1-yl)-[7-(2-methyl-1H-indol-5-yloxy)-thieno[3,2-b]pyridin-2-yl]-methanone (85 mg, 0.2 mmol) in DMF (5 mL), at 0° C. The reaction mixture was allowed to stir for 20 min, and EtI (57 mg, 0.40 mmol) was added dropwise. After 3 h the reaction was quenched with saturated aqueous KCN (10 mL). The aqueous layer was extracted with $CH_2Cl_2$ (3×15 mL). The combined organic extracts were dried ($Na_2SO_4$), and the solvent was removed. Purification by flash chromatography on silica gel ($CH_2Cl_2$/MeOH 94:6) afforded the title compound as a white solid (46 mg, 51%). MS: 450 (MH+); HPLC Rf: 6.83 min; HPLC purity: 95%.

EXAMPLE 11

(2R)-[7-(1,2-Dimethyl-1H-indol-5-yloxy)-thieno[3,2-b]pyridin-2-yl]-(2-methoxymethyl-pyrrolidin-1-yl)-methanone The title compound was prepared by the method described for Example 10, using (2R)-(2-methoxymethyl-pyrrolidin-1-yl)-[7-(2-methyl-1H-indol-5-yloxy)-thieno[3,2-b]pyridin-2-yl]-methanone and methyl iodide. MS: 436 (MH+); HPLC Rf: 6.33 min; HPLC purity: 96%.

EXAMPLE 12

(2R)-1-{5-[2-(2-Methoxymethyl-pyrrolidine-1-carbonyl)-thieno[3,2-b]pyridin-7-yloxyl]-2-methyl-indol-1-yl-ethanone To a solution of (2R)-(2-methoxymethyl-pyrrolidin-1-yl)-[7-(2-methyl-1H-indol-5-yloxy)-thieno[3,2-b]pyridin-2-yl]-methanone and DMAP (120 mg, 0.28 mmol) in DMF (5 mL) was added acetyl chloride (44 mg, 0.56 mmol). After 3 h the reaction was quenched with water (5 mL). The aqueous layer was extracted with $CH_2Cl_2$ (2×15 mL). The combined organic extracts were dried ($Na_2SO_4$), and concentrated onto silica gel (5 mL). Purification by flash chromatography on silica gel ($CH_2Cl_2$/MeOH 97:3) afforded the title compound as a white solid (0.36 g, 69%). MS: 464 (MH+); HPLC Rf: 6.12 min; HPLC purity: 96%.

EXAMPLE 13

(2R)-R[7-(1-Methanesulfonyl-2-methyl-1H-indol-5-yloxy)-thieno[3,2-b]pyridin-2-yl]-(2-methoxymethyl-pyrrolidin-1-l)-methanone The title compound was prepared by the method described for Example 12 from (2R)-(2-methoxymethyl-pyrrolidin-1-yl)-[7-(2-methyl-1H-indol-5-yloxy)-thieno[3,2-b]pyridin-2-yl]-methanone and methanesulfonyl chloride. MS: 501 (MH+); HPLC Rf: 6.13 min; HPLC purity: 97%.

EXAMPLE 14

2-(3-Methyl-3H-imidazol-4-yl)-7-(2-methyl-1H-indol-5-yloxy)-thieno[3,2-b]pyridine A. 7-Chloro-2-(3-methyl-3H-imidazol-4-yl)-thieno[3,2-b]pyridine The title compound was prepared by the method described in PCT application WO-99/24440. Example 148. MS: 361 (MH+); HPLC Rf: 5.37 min; HPLC purity: 98%.

B. 2-(3-Methyl-3H-imidazol-4-yl)-7-(2-methyl-1H-indol-5-yloxy)-thieno[3,2-b]pyridine The title compound was prepared by the method described for Example 1F. MS: 361 (MH+); HPLC Rf: 5.94 min; HPLC purity: 99%.

EXAMPLE 15

2-(1-Methyl-1H-imidazol-2-yl)-7-(2-methyl-1H-indol-5-yloxy)-thieno[3,2-b]pyridine A. 7-Chloro-2-(1-methyl-1H-imidazol-2-yl)-thieno[3,2-b]pyridine The title compound was prepared by the method described in PCT application WO-99/24440, Example 149. MS: 251 (MH+); HPLC Rf: 5.02 min; HPLC purity: 95%.

B. 2-(1-Methyl-1H-imidazol-2-yl)-7-(2-methyl-1H-indol-5-yloxy)-thieno[3,2-b]pyridine The title compound was prepared by the method described for Example 1F. MS: 361 (MH+); HPLC RM: 5.61 min; HPLC purity: 97%.

EXAMPLE 16

2-{2-[7-(2-Methyl-1H-indol-5-yloxy)-thieno[3,2-b]pyridin-2-yl]-thiazol-4-yl}-propan-2-ol A. 7-Chloro-thieno[3,2-b]pyridine-2-carbothioic acid methoxymethyl amide Solid 7-chloro-thieno[3,2-b]pyridine (60 g, 360 mmol) was added with stirring to 600 mL dry THF. Nitrogen was bubbled through the solution for ten minutes then cooled to −78° C. n-Butyl lithium (170 mL, 432 mmol) (2.5 M solution in hexanes) was added drop-wise at a rate such that the temperature is maintained below −65° C. The reaction mixture was stirred at −78° C. for three hours. Methoxymethyl isothiocyanate (43.2 mL, 468 mmol) in 400 mL THF was slowly added. Complete solution was noted after the addition was complete. The reaction mixture was then allowed to stir at −78° C. for three hours. The reaction mixture was removed from the cooling bath and 150 mL saturated $NH_4Cl$ solution was added. The reaction mixture turned a bright yellow color. THF was removed under reduced pressure, and 7-Chloro-thieno[3,2-b]pyridine-2-carbothioic acid methoxymethyl amide was filtered, washed with ethyl acetate and dried giving 93.7 g, a 95% yield as a yellow-orange solid. $C_{10}H_9ClN_2OS_2$: APCI m/z 273.0/274.9 (MH+).); $^1$H NMR ($d_6$-DMSO): δ 8.60 (d, 1H, J=5.0 Hz), 8.13 (s, 1H), 7.55 (d, 1H, J=5.0 Hz), 4.97 (s, 2H), 2.46 (s, 3H) ppm.

B. 7-chloro-thieno[3,2-b]pyridine-2-carbothioic acid amide

To a solution of 7-Chloro-thieno[3,2-b]pyridine-2-carbothioic acid methoxymethyl-amide (93.9 g, 344 mmol) and 900 mL THF was added 1 N HCl (344 mL, 344 mmol). The reaction mixture was heated to reflux for seventy-two hours. The reaction mixture was cooled to 0° C., and 300 mL of concentrated $NH_4OH$ was added and stirred. The THF was removed under reduced pressure and the residue was suspended in ethyl acetate and stirred. The precipitate was filtered, washed with ethyl acetate and dried to give 7-chloro-thieno[3,2-b]pyridine-2-carbothioic acid amide (66.7 g) in 85% yield. $C_8H_5ClN_2S_2$: APCI m/z: 228.9/230.9 (MH+); $^1$H NMR ($d_6$-DMSO): δ 10.24 (s, 1H), 9.94 (s, 1H), 8.65 (d, 1H, J=5.0 Hz), 8.19 (s, 1H), 7.62 (d, 1H, J=5.0 Hz) ppm.

C. 2-(7-Chloro-thieno[3,2-b]pyridin-2-yl)-thiazole-4-carboxylic acid ethyl ester To a solution of 7-Chloro-thieno[3,2-b]pyridine-2-carbothioic acid amide (5.00 g, 21.9 mmol) in 60 mL of THF was added ethyl bromopyruvate (4.11 mL, 32.8 mmol). The reaction mixture was stirred at room temperature under nitrogen overnight. The reaction mixture was cooled to 0° C., and 30 mL trifluoroacetic anhydride was added. The reaction was stirred at room temperature for four hours then cooled to 0° C. The reaction was treated with 30 mL of concentrated $NH_4OH$ followed by removal of THF under reduced pressure. The dark, oily residue was partitioned between water and ethyl acetate. The aqueous layer was separated and washed with ethyl acetate. The combined organic layers were washed with brine, dried over magnesium sulfate, and evaporated under reduced pressure to give a brown oily residue. Chromotography (99.5:0.45:0.05 $CHCl_3$:$CH_3OH$:$NH_4OH$) over silica gel gave a 67% of 2-(7-Chloro-thieno[3,2-b]pyridin-2-yl)-thiazole-4-carboxylic acid ethyl ester (3.42 g) as a pale yellow solid. $C_{13}H_9ClN_2O_2S_2$: APCI m/z 325.0/327.0 (MH+); 232.9/325.9 (neg.); $^1$H NMR ($d_6$-DMSO): δ 8.67 (d, 1H, J=5.0 Hz), 8.37 (s, 1H), 7.62 (d, 1H, J=5.0 Hz), 3.98 (q, 2H, J=7.0 Hz), 1.13 (t, 3H, J=7.0 Hz) ppm.

D. 2-[2-(7-Chloro-thieno[3,2-b]pyridin-2-yl)-thiazol-4-yl]-propan-2-ol

To a solution of 2-(7-Chloro-thieno[3,2-b]pyridin-2-yl)-thiazole-4-carboxylic acid ethyl ester (220 mg, 0.677 mmol) in 3.0 mL dry THF cooled to −78° C. was added methyl magnesium bromide (3.0 M in THF) (564 μL, 1.69 mmol). The reaction was stirred at −78° C. for four hours, removed from the cooling bath and quenched with 1 mL of saturated $NH_4Cl$ solution. The reaction was extracted with ethyl acetate and saturated $NaHCO_3$. The aqueous layer was washed with ethyl acetate. The combined organic layers were washed with brine, dried over magnesium sulfate, and evaporated under reduced pressure giving a brown solid. Silica gel chromatography (98:1.8:0.2 $CHCl_3$:$CH_3OH$:$NH_4OH$) of the residue gave a 48% yield of 2-[2-(7-Chloro-thieno[3,2-b]pyridin-2-yl)-thiazol-4-yl]-propan-2-ol (0.1 g) as a yellow solid. $C_{13}H_{11}ClN_2OS_2$ $C_{13}H_{11}ClN_2OS_2$: APCI m/z 311.1/313.1 (MH+); $^1$H NMR ($d_6$-DMSO) δ 8.67 (d, 1H, J=5.4 Hz), 8.20 (s, 1H), 7.61 (d, 1H, J=5.4 Hz), 7.60 (s, 1H), 1.48 (s, 6H) ppm.

E. 2-methyl-1H-indol-5-ol

A solution of 5-Methoxy-2-methyl-1H-indole (2 g, 12.4 mmol) in 10 mL dichloromethane was cooled to −78° C. A 1.0 M solution of $BBr_3$ in dichloromethane (30 mL, 30.0 mmol) was added and the resultant mixture was stirred at −78° C. for three hours. The reaction was carefully quenched into ice water and extracted with dichloromethane two times. The combined organic layers were washed with brine, dried over magnesium sulfate, and evaporated under reduced pressure to give a dark oil. Silica gel chromatography (98:1.8:0.2 $CHCl_3$:$CH_3OH$:$NH_4OH$) of the residue gave a 60% yield of 2-methyl-1H-indol-5-ol (1.09 g) as a tan solid. $C_9H_9NO$: GC/MS: r.t.=2.88 min., m/z 146. $^1$H NMR ($CD_3OD$): δ 7.03 (d, 1H, J=8.7 Hz), 6.77 (s, 1H), 6.53 (D, 1H, J=8.7 Hz), 5.92 (s, 1H), 2.32 (s, 3H) ppm.

F. 2-{2-[7-(2-Methyl-1H-indol-5-yloxy-thieno[3,2-b]pyridin-2-yl]-thiazol-4-yl}-propan-2-ol A solution of 2-[2-(7-Chloro-thieno[3,2-b]pyridin-2-yl)-thiazol-4-yl]-propan-2-ol (100 mg, 0.322 mmol), DMF 0.7 mL, cesium carbonate (210 mg, 0.644 mmol) and 2-methyl-1H-indol-5-ol and (95.0 mg, 0.644 mmol) was heated to 85° C. for sixteen hours. The reaction mixture was cooled to room temperature and extracted with 5% methanol/ethyl acetate and water. The layers were separated, and the aqueous layer was washed with a 5% methanol and ethyl acetate solution. The combined organic layers were washed with brine, dried over magnesium sulfate, and evaporated under reduced pressure to give an oily brown solid. Silica gel chromatography (98:1.8:0.2 $CHCl_3$:$CH_3OH$:$NH_4OH$) afforded the titled compound (46 mg) as an off-white solid in 17% yield. $C_{22}H_{19}N_3O_2S_2$: APCI m/z 422.2 (pos.); $^1$H NMR ($CD_3OD$): δ 8.38 (d, 1H, J=5.6 Hz), 7.89 (s, 1H), 7.47 (s, 1H), 7.35 (d, 1H, J=8.7 Hz), 7.26 (s, 1H), 6.87 (d, 1H, J=8.7 Hz), 6.57 (d, 1H, J=5.6 Hz), 6.17 (s, 1H), 2.43 (s, 3H), 1.61 (s, 6H) ppm.

EXAMPLE 17

2-{2-[7-(2-Methyl-quinolin-6-)yloxy)-thieno[3,2-b]pyridin-2-yl]-thiazol-4-yl}-propan-2-ol The title compound (23 mg, 16%) was prepared from 2-[2-(7-Chloro-thieno[3,2-b]pyridin-2-yl)-thiazol-4-yl]-propan-2-ol and 2-methylquinolin-6-ol by a procedure analogous to Example 16. $C_{23}H_{19}N_3O_2S_2$: APCI m/z 434.2 (pos.); HPLC r.t.=6.406 min.; $^1$H NMR ($CD_3OD$): δ 8.48 (d, 1H, J=5.4 Hz), 8.24 (d, 1H, J=8.4 Hz), 8.08 (d, 1H, J=9.1 Hz), 7.92 (s, 1H), 7.77 (s, 1H), 7.66 (d, 1H, J=9.1 Hz), 7.48 (d, 1H, J=8.4 Hz), 7.48 (s, 1H), 6.76 (d, 1H, J=5.4 Hz), 2.73 (s, 3H), 1.60 (s, 6H) ppm.

EXAMPLE 18

2-{2-[7-(Quinolin-6-yloxy)-thieno[3,2-b]pyridin-2-yl]-thiazol-4-}-propan-2-ol

The title compound (9 mg, 7%) was prepared from 2-[2-(7-Chloro-thieno[3,2-b]pyridin-2-yl)-thiazol-4-yl]-propan-2-ol and quinolin-6-ol by a procedure analogous to Example 16. $C_{22}H_{17}N_3O_2S_2$: APCI m/z 420.2 (MH+); $^1$H NMR (CD$_3$OD): δ 8.87 (d, 1H, J=4.3 Hz), 8.48 (d, 1H, J=5.4 Hz), 7.91 (s, 1H), 7.81 (s, 1H), 7.70 (d, 1H, J=9.1 Hz), 7.57 (dd, 1H, J=9.1, 4.3 Hz), 7.47 (s, 1H), 6.77 (d, 1H, J=5.4 Hz), 1.59 (s, 6H) ppm.

EXAMPLE 19

2-{2-[7-(1-Methyl-5-trifluoromethyl-1H-pyrazol-3-yloxy)-thieno[3,2-b]pyridin-2-yl]-thiazol-4-yl}-propan-2-ol The title compound (11 mg, 8%) was prepared from 2-[2-(7-chloro-thieno[3,2-b]pyridin-2-yl)-thiazol-4-yl]-propan-2-ol and 1-methyl-5-trifluoromethyl-1H-pyrazol-3-ol by a procedure analogous to Example 16. $C_{18}H_{15}F_3N_4O_2S_2$: APCI m/z 441.3 (pos.); $^1$H NMR (CD$_3$OD): δ 8.53 (d, 1H, J=5.6 Hz), 7.91 (s, 1H), 7.48 (s, 1H), 7.07 (d, 1H, J=5.6 Hz), 6.68 (s, 1H), 3.98 (s, 3H), 1.61 (s, 6H) ppm.

EXAMPLE 20

{4-Methyl-2-[7-(2-methyl-1H-indol-5-yloxy)-thieno[3,2-b]pyridin-2-yl]-thiazol-5-yl}-(4-methyl-piperazin-1-yl)-methanone A. 2-(7-Chloro-thieno[3,2-b]pyridin-2-yl)-4-methyl-thiazole-5-carboxylic acid ethyl ester 19.5 g (85.6 mmol) of 7-chloro-thieno[3,2-b]pyridine-2-carbothioic acid amide was added to 160 mL of a 1:1 DMF:THF solution mixture and cooled to 0° C. To this solution was slowly added 17.7 mL (128 mmol) of ethyl 2-chloroacetoacetate. After addition, the reaction was heated to 80° C. for sixteen hours. The reaction was cooled to room temperature and extracted with dichloromethane and water. The organic layer was separated and dried over magnesium sulfate, filtered, concentrated and purified by silica gel chromatography to afford 2-(7-Chloro-thieno[3,2-b]pyridin-2-yl)-4-methyl-thiazole-5-carboxylic acid ethyl ester (15.6 g) in 54% yield. $C_{14}H_{11}ClN_2O_2S_2$: APCI m/z 339.1/341.0 (pos.); $^1$H NMR (CDCl$_3$): δ 8.68 (d, 1H, J=5.4 Hz), 8.24 (s, 1H), 7.51 (d, 1H, J=5.4 Hz), 4.36 (q, 2H, J=7.1 Hz), 2.77 (s, 3H), 1.38 (t, 3H, J=7.1 Hz) ppm.

B. 2-(7-chloro-thieno[3,2-b]pyridin-2-yl)-4-methyl-thiazole-5-carboxylic acid

To a solution of 15.2 g (46.2 mmol) 2-(7-chloro-thieno[3,2-b]pyridin-2-yl)-4-methyl-thiazole-5-carboxylic acid ethyl ester, 80 mL of THF and 20 mL of absolute ethanol was added (13 g, 231 mmol) freshly ground potassium hydroxide. The reaction was stirred at room temperature for sixteen hours. The reaction was cooled to 0° C. and the pH was adjusted to pH 3 with conc HCl. The resulting yellow precipitate was filtered and dried to give 2-(7-chloro-thieno[3,2-b]pyridin-2-yl)-4-methyl-thiazole-5-carboxylic acid (10.3 g) in 72% yield. $C_{12}H_7N_2O_2S_2$: APCI m/z 310.2/312.2 (pos.); $^1$H NMR (d$_6$-DMSO): δ 8.67 (d, 1H, J=5.0 Hz), 8.42 (s, 1H), 7.65 (d, 1H, J=5.0 Hz), 2.65 (s, 3H) ppm.

C. 2-(7-chloro-thieno[3,2-b]pyridin-2-yl)-4-methyl-thiazole-5-carbonyl Chloride

To a solution of 4 g (12.9 mmol) of 2-(7-chloro-thieno[3,2-b]pyridin-2-yl)-4-methyl-thiazole-5-carboxylic acid 40 mL of 1,2-dichloroethane and 0.1 mL dimethyl formamide was carefully added 4.7 mL (64.4 mmol) of thionyl chloride. The reaction was heated to 90° C. for five hours. The reaction was cooled to room temperature and dry ethyl ether was added. The resulting brown precipitate was collected by vacuum filtration, washed with diethyl ether and dried to afford 2-(7-chloro-thieno[3,2-b]pyridin-2-yl)-4-methyl-thiazole-5-carbonyl chloride (3.31 g) in 78% yield. $C_{12}H_6Cl_2N_2OS_2$: APCI m/z (in methanol to give methyl ester) 325.1/327.1 (pos.); $^1$H NMR (d$_6$-DMSO): δ 8.68 (d, 1H, J=5.0 Hz), 8.32 (s, 1H), 8.65 (d, 1H, J=5.0 Hz), 2.39 (s, 3H) ppm.

D. [2-(7-Chloro-thieno[3,2-b]pyridin-2-yl)-4-methyl-thiazol-5-yl]-(4-methyl-piperazin-1-yl)-methanone A solution of 2-(7-Chloro-thieno[3,2-b]pyridin-2-yl)-4-methyl-thiazole-5-carbonyl chloride, (0.28 g, 0.85 mmol), dry dichloromethane (1.5 mL), and 1-methylpiperazine (0.21 mL, 1.87 mmol) was stirred at room temperature for four hours. A gas discharge and immediate solution were noted. The reaction mixture was evaporated directly onto silica gel and purified through silica gel chromatography to afford [2-(7-Chloro-thieno[3,2-b]pyridin-2-yl)-4-methyl-thiazol-5-yl]-(4-methyl-piperazin-1-yl)-methanone (0.234 g) in 70% yield. $C_{17}H_{17}ClN_4OS_2$: APCI 393.2/395.2 (pos.); $^1$H NMR (d$_6$-DMSO): δ 8.68 (d, 1H, J=5.4 Hz), 8.32 (s, 1H), 7.64 (d, 1H, J=5.4 Hz), 3.6–3.4 (bm, 4H), 2.38 (s, 4H), 2.4–2.2 (bm, 4H), 2.17 (s, 3H) ppm.

E. {4-Methyl-2-[7-(2-methyl-1H-indol-5-yloxy)-thieno[3,2-b]pyridin-2-yl]-thiazol-5-yl}-(4-methyl-piperazin-1-yl)-methanone The title compound (77 mg, 51%) was prepared from [2-(7-Chloro-thieno[3,2-b]pyridin-2-yl)-4-methyl-thiazol-5-yl]-(4-methyl-piperazin-1-yl)-methanone and 2-methyl-1H-indol-5-ol by a procedure analogous to Example 16 as a tan colored hydrochloride salt. $C_{26}H_{25}N_5O_2S_2$: APCI m/z 504.3 (pos.); $^1$H NMR (CD$_3$OD): δ 8.46 (d, 1H, J=5.4 Hz), 7.99 (s, 1H), 7.35 (d, 1H, J=8.3 Hz), 7.26 (s, 1H), 6.87 (d, 1H, J=8.3 Hz), 6.67 (d, 1H, J=5.4 Hz), 6.17 (s, 1H), 3.8–3.0 (bm, 8H), 2.95 (s, 3H), 2.49 (s, 3H), 2.43 (s, 3H) ppm.

EXAMPLE 21

2-Methyl-5-{2-[4-methyl-5-(4-methyl-piperazine-1-carbonyl)-thiazol-2-yl]-thieno[3,2-b]pyridin-7-yloxy}-1H-indole-3-carbonitrile A. 5-methoxy-2-methyl-1H-indole-3-carbonitrile To a 0° C. solution of 5-Methoxy-2-methyl-1H-indole (5 g, 31.0 mmol), dry acetonitrile, (90 mL) was slowly added chlorosulfonyl isocyanate (3 mL, 34.1 mmol). The reaction was stirred and allowed to warm to room temperature and stirred for an additional four hours followed by the addition of dimethyl formamide (4.8 mL (62.0 mmol)and then stirred for an additional 1.5 hours at room temperature. The reaction was poured into water and extracted with diethyl ether. The aqueous layer was adjusted to pH 9 with 1M potassium carbonate, and extracted with diethyl ether. The ether layers were combined and dried over magnesium sulfate, filtered and concentrated. Crystallization of the residue from ether and hexane gave 5-methoxy-2-methyl-1H-indole-3-carbonitrile (3.86 g) in 67% yield as a light pink solid. $C_{11}H_{10}N_2O$: GC/MS r.t.=4.06 min., m/z 186; $^1$H NMR (CDCl$_3$): δ 7.22 (d, 1H, J=8.3 Hz), 7.08 (s, 1H), 6.86 (d, 1H, J=8.3 Hz), 3.86 (s, 3H), 2.60 (s, 3H) ppm.

B. 5-methoxy-2-methyl-1H-indole-3-carbonitrile

5-Hydroxy-2-methyl-1H-indole-3-carbonitrile (1.69 g, 61%) was prepared as a white solid after chromatography from 5-methoxy-2-methyl-1H-indole-3-carbonitrile by a procedure analogous to Example 16E. $C_{10}H_8N_2O$: GC/MS, m/z 172; $^1$H NMR (DMSO): δ 11.8 (s, 1H), 9.1 (s, 1H), 7.20 (d, 1H, J=8.8 Hz), 6.78 (s, 1H), 6.67 (d, 1H, J=8.8 Hz), 2.46 (s, 3H) ppm.

C. 2-Methyl-5-{2-[4-methyl-5-(4-methyl-piperazine-1-carbonyl)-thiazol-2-yl]-thieno[3,2-b]pyridin-7-yloxy}-1H-indole-3-carbonitrile The title compound (61 mg, 41%) was prepared from [2-(7-Chloro-thieno[3,2-b]pyridin-2-yl)-4-methyl-thiazol-5-yl]-(4-methyl-piperazin-1-yl)-methanone and 5-Hydroxy-2-methyl-1 H-indole-3-carbonitrile by a procedure analogous to Example 16 using and in a 41% yield. $C_{27}H_{25}N_6O_2S_2$: APCI m/z 529.4 (pos.); $^1$H NMR (CD$_3$OD): δ 8.72 (d, 1H, J=6.6 Hz), 8.17 (s, 1H), 7.60 (d, 1H, J=8.7 Hz), 7.58 (s, 1H), 7.23 (d, 1H, J=8.7 Hz), 7.07 (d, 1H, J=6.6 Hz), 3.65–3.15 (bm, 8H), 2.96 (s, 3H), 2.63 (s, 3H), 2.52 (s, 3H) ppm.

EXAMPLE 22

{4-Methyl-2-[7-(5-phenyl-1H-pyrazol-3-yloxy)-thieno[3,2-b]pyridin-2-yl]-thiazol-5-yl}-morpholin-4-yl-methanone A. 5-Phenyl-1,2-dihydro-pyrazol-3-one A vigorously stirred solution of ethyl benzoylacetate (30 g 150 mmol), of 5% aqueous sodium hydroxide (312 mL), and hydrazine hydrate (14.6 mL 468 mmol) was heated to 75° C. for sixteen hours. The resultant precipitate was filtered, washed with water and dried and gave 5-Phenyl-1,2-dihydro-pyrazol-3-one (20.3) in 81% yield as a white solid. $C_9H_8N_2O$: $^1$H NMR (d$_6$-DMSO): δ 7.62 (d, 2H, J=7.0 Hz), 7.36 (t, 2H, J=7.0 Hz), 7.26 (t, 1H, J=7.0 Hz), 5.85 (s, 1H) ppm.

B. [2-(7-Chloro-thieno[3,2-b]pyridin-2-yl)-4-methyl-thiazol-5-yl]-morpholin-4-yl-methanone

[2-(7-Chloro-thieno[3,2-b]pyridin-2-yl) -4-methyl-thiazol-5-yl]-morpholin-4-yl-methanone (532 mg, 82%) was prepared from 2-(7-Chloro-thieno[3,2-b]pyridin-2-yl)-4-methyl-thiazole-5-carbonyl chloride and morpholine in a procedure analogous to Example 20. $C_{16}H_{14}ClN_3O_2S_2$: APCI m/z 380.0/382.1 (pos.).

C. {4-Methyl-2-[7-(5-phenyl-1H-pyrazol-3-yloxy)-thieno[3,2-b]pyridin-2-yl]-thiazol-5-yl}-morpholin-4-yl-methanone The title compound (37 mg, 17%) was prepared from [2-(7-Chloro-thieno[3,2-b]pyridin-2-yl)-4-methyl-thiazol-5-yl]-morpholin-4-yl-methanone and 5-Phenyl-1,2-dihydro-pyrazol-3-one by a procedure analogous to Example 16 1. $C_{25}H_{21}N_5O_3S_2$: APCI m/z 503.5 (pos.); $^1$H NMR (CD$_3$OD): δ 8.55 (d, 1H, J=5.8 Hz), 8.00 (s, 1H), 7.72 (d, 2H, J=7.1 Hz), 7.46 (t, 2H, J=7.1 Hz), 7.41 (t, 1H, J=7.1 Hz), 7.08 (d, 1H, J=5.8 Hz), 6.53 (s, 1H), 3.71–3.60 (bm, 8H), 2.46 (s, 3H) ppm.

EXAMPLE 23

(2-{7-[5-(4-Fluoro-phenyl)-1H-pyrazol-3-yloxy]-thieno[3,2-b]pyridin-2-yl}-4-methyl-thiazol-5-yl)-(4-methyl-piperazin-1-yl)-methanone A. 5-(4-Fluoro-phenyl)-1H-pyrazol-3-ol 5-(4-Fluoro-phenyl)-1H-pyrazol-3-ol (7.67 g, 84%) was prepared as a white solid from 3-(4-Fluoro-phenyl)-3-oxo-propionic acid methyl ester (10.0 g, 51.0 mmol) and hydrazine (4.76 mL, 153 mmol) by a procedure analogous to Example 22. $C_9H_7FN_2O$: $^1$H NMR (d$_6$-DMSO): δ 7.66 (dd, 2H, $J_{CH-CF}$=11.7 Hz, $J_{CH-CH}$=8.7 Hz), 7.21 (d, 2H, J=8.7 Hz), 5.83 (s, 1H) ppm.

B. (2-{7-[5-(4-Fluoro-phenyl)-1H-pyrazol-3-yloxy]-thieno[3,2-b]pyridin-2-yl}-4-methyl-thiazol-5-yl)-(4-methyl-piperazin-1-yl)-methanone The title compound (36.4 mg, 17%) was prepared from [2-(7-Chloro-thieno[3,2-b]pyridin-2-yl)-4-methyl-thiazol-5-yl]-morpholin-4-yl-methanone and 5-(4-Fluoro-phenyl)-1H-pyrazol-3-ol by a procedure analogous to Example 22. $C_{26}H_{23}FN_6O_2S_2$: APCI m/z 535.0 (MH+); $^1$H NMR (CD$_3$OD): δ 8.84 (d, J=6.6 Hz, 1H), 8.20 (s, 1H), 7.78 (dd, $J_{CH-CF}$=11.8 Hz, $J_{CH-CH}$=8.8 Hz, 2H), 7.61 (d, J=6.6 Hz, 1H), 7.25 (d, J=8.8 Hz, 2H), 6.64 (s, 1H), 3.6–3.1 (bm, 8H), 2.96 (s, 3H), 2.53 (s, 3H) ppm.

EXAMPLE 24

2-{7-[5-(4-Methoxy-phenyl)-1H-pyrazol-3-yloxy]-thieno[3,2-b]pyridin-2-yl}-4-methyl-thiazol-5-yl)-(4-methyl-piperazin-1-yl)-methanone A. 5-(4-Methoxy-phenyl)-1H-pyrazol-3-ol 5-(4-Methoxy-phenyl)-1H-pyrazol-3-ol (30.8 g, 99%) was prepared as a white solid from 3-(4-methoxy-phenyl)-3-oxo-propionic acid ethyl ester (29.9 mL, 156 mmol) and hydrazine hydrate (14.6 mL, 468 mmol) by a procedure analogous to Example 22. $C_{10}H_{10}N_2O_2$: $^1$H NMR (D$_6$-DMSO): δ 7.55 (d, J=8.8 Hz, 2H), 6.93 (d, J=8.8 Hz, 2H), 5.75 (s, 1H), 3.73 (s, 3H) ppm.

B. 2-{7-[5-(4-Methoxy-phenyl)-1H-pyrazol-3-yloxy]-thieno[3,2-b]pyridin-2-yl}-4-methyl-thiazol-5-yl)-(4-methyl-piperazin-1-yl)-methanone The title compound (8 mg, 4%) was prepared from 5-(4-methoxy-phenyl)-1H-pyrazol-3-ol (109 mg, 0.573 mmol) and [2-(7chloro-thieno[3,2-b]pyridin-2-yl)-4-methyl-thiazol-5-yl]-morpholin-4-yl-methanone (150 mg, 0.382 mmol) by a procedure analogous to Example 16. $C_{27}H_{26}N_6O_3S_2$: APCI m/z 547.0 (MH+); $^1$H NMR (CDCl$_3$): δ 8.52 (d, J=5.4 Hz, 1H), 7.85 (s, 1H), 7.48 (d, J=8.7 Hz, 2H), 7.00 (d, J=5.4 Hz, 1H), 6.86 (d, J=8.7 Hz, 2H), 6.18 (s, 1H), 3.77 (s, 3H), 3.80–3.55 (bm, 8H), 2.46 (s, 3H), 2.32 (s, 3H) ppm.

What is claimed is:

1. A compound of the formula 1 or 2

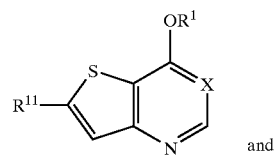

and

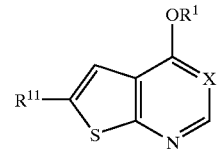

or a pharmaceutically acceptable salts or solvates thereof, wherein X is CH;

$R^1$ is H, $C_1$–$C_6$ alkyl, —C(O)($C_1$–$C_6$ alkyl), $C_6$–$C_{10}$ aryl or 5 to 13 membered heterocyclic, wherein said $C_6$–$C_{10}$ aryl and 5 to 13 membered heterocyclic groups are optionally substituted by 1 to 5 $R^5$ substituents;

each $R^5$ is independently selected from halo, cyano, nitro, trifluoromethoxy, trifluoromethyl, azido, —C(O)$R^8$, —C(O)O$R^8$, —OC(O)$R^8$, —OC(O)O$R^8$, —N$R^6$C(O) $R^7$, —C(O)N$R^6R^7$, —N$R^6R^7$, —O$R^9$, —SO$_2$N$R^6R^7$, $C_1$–$C_6$ alkyl, —(CH$_2$)$_j$O(CH$_2$)$_q$N$R^6R^7$, —(CH$_2$)$_t$O (CH$_2$)$_q$O$R^9$, —(CH$_2$)$_t$O$R^9$, —S(O)$_j$($C_1$–$C_6$ alkyl), —(CH$_2$)$_t$($C_6$–$C_{10}$ aryl), —(CH$_2$)$_t$(5 to 10 membered heterocyclic), —C(O)(CH$_2$)$_t$($C_6$–$C_{10}$ aryl), —(CH$_2$)$_t$O (CH$_2$)$_t$($C_6$–$C_{10}$aryl), —(CH$_2$)$_t$O(CH$_2$)$_t$(5 to 10 membered heterocyclic), —C(O)(CH$_2$)$_t$(5 to 10 membered heterocyclic), —(CH$_2$)$_j$N$R^7$(CH$_2$)$_q$N$R^6R^7$, —(CH$_2$)$_j$N$R^7$CH$_2$C(O)N$R^6R^7$, —(CH$_2$)$_j$N$R^7$(CH$_2$)$_q$N$R^9$C(O) $R^8$, —(CH$_2$)$_j$N$R^7$(CH$_2$)$_t$O(CH$_2$)$_q$O$R^9$, —(CH$_2$)$_j$N$R^7$ (CH$_2$)$_q$S(O)$_j$($C_1$–$C_6$ alkyl), —(CH$_2$)$_j$N$R^7$(CH$_2$)$_t$$R^6$, —SO$_2$(CH$_2$)$_t$($C_6$–$C_{10}$ aryl), and —SO$_2$(CH$_2$)$_t$(5 to 10 membered heterocyclic), wherein j is an integer from 0 to 2, t is an integer from 0 to 6, q is an integer from 2 to 6, the —(CH$_2$)$_q$— and —(CH$_2$)$_t$— moieties of the foregoing $R^5$ groups optionally include a carbon-carbon double or triple bond where t is an integer between 2 and 6, and the alkyl, aryl and heterocyclic moieties of the foregoing $R^5$ groups are optionally substituted by 1 to 3 substituents independently selected from halo, cyano, nitro, trifluoromethyl, azido, —C(O)$R^8$, —C(O) O$R^8$, —OC(O)$R^8$, —OC(O)O$R^8$, —N$R^6$C(O)$R^7$, —C(O)N$R^6R^7$, —(CH$_2$)$_t$N$R^6R^7$, $C_1$–$C_6$ alkyl, —(CH$_2$)$_t$ ($C_6$–$C_{10}$ aryl), —(CH$_2$)$_t$(5 to 10 membered heterocyclic), —(CH$_2$)$_t$O(CH$_2$)$_q$O$R^9$, and —(CH$_2$)$_t$ O$R^9$, wherein t is an integer from 0 to 6 and q is an integer from 2 to 6;

each $R^6$ and $R^7$ is independently selected from H, $C_1$–$C_6$ alkyl, —(CH$_2$)$_t$($C_6$–$C_{10}$ aryl), —(CH$_2$)$_t$(5 to 10 membered heterocyclic), —(CH$_2$)$_t$O(CH$_2$)$_q$O$R^9$, and —(CH$_2$)$_t$O$R^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, nitro, trifluoromethyl, azido, —C(O)$R^8$, —C(O)O$R^8$, —CO(O)$R^8$, —OC(O)O$R^8$, —N$R^9$C(O)$R^{10}$, —C(O)N$R^9R^{10}$, —N$R^9R^{10}$, $C_1$–$C_6$ alkyl, —(CH$_2$)$_t$($C_6$–$C_{10}$ aryl), —(CH$_2$)$_t$(5 to 10 membered heterocyclic), —(CH$_2$)$_t$O (CH$_2$)$_q$O$R^9$, and —(CH$_2$)$_t$O$R^9$, wherein t is an integer from 0 to 6 and q is an integer from 2 to 6, with the proviso that where $R^6$ and $R^7$ are both attached to the same nitrogen, then $R^6$ and $R^7$ are not both bonded to the nitrogen directly through an oxygen;

each $R^8$ is independently selected from H, $C_1$–$C_{10}$ alkyl, —(CH$_2$)$_t$($C_6$–$C_{10}$ aryl), and —(CH$_2$)$_t$(5 to 10 membered heterocyclic), wherein t is an integer from 0 to 6;

each $R^9$ and $R^{10}$ is independently selected from H and $C_1$–$C_6$ alkyl; and, $R^{11}$ is $C_1$–$C_6$ alkyl, —C(O)N$R^{12}R^{13}$, —C(O)($C_6$–$C_{10}$ aryl), —(CH$_2$)$_t$($C_6$–$C_{10}$ aryl), —(CH$_2$)$_t$(5 to 10 membered heterocyclic), —(CH$_2$)$_t$N$R^{12}R^{13}$, —SO$_2$N$R^{12}R^{13}$ and —CO$_2$$R^{12}$, wherein t is an integer from 0 to 6, wherein said $R^{11}$ groups $C_1$–$C_6$ alkyl, —C(O)($C_6$–$C_{10}$ aryl), —(CH$_2$)$_t$($C_6$–$C_{10}$ aryl), and —(CH$_2$)$_t$(5 to 10 membered heterocyclic) are optionally substituted by 1 to 5 $R^5$ groups, and wherein each $R^{12}$ and $R^{13}$ is independently selected from H, $C_1$–$C_6$ alkyl, —(CH$_2$)$_t$ ($C_3$–$C_{10}$ cycloalkyl), —(CH$_2$)$_t$($C_6$–$C_{10}$ aryl), —(CH$_2$)$_t$ (5 to 10 membered heterocyclic), —(CH$_2$)$_t$O(CH$_2$)$_q$ O$R^9$, and —(CH$_2$)$_t$O$R^9$, q is an integer from 2 to 6, and the alkyl, aryl and heterocyclic moieties of the forego- ing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

2. A compound of claim 1, wherein $R^{11}$ is —(CH$_2$)$_t$(5 to 10 membered heterocyclic), —C(O)N$R^{12}R^{13}$, —(CH$_2$)$_t$ N$R^{12}R^{13}$, —SO$_2$N$R^{12}R^{13}$ and —CO$_2$$R^{12}$, wherein t is an integer from 0 to 6, wherein said $R^{11}$ group —(CH$_2$)$_t$(5 to 10 membered heterocyclic) is optionally substituted by 1 to 5 $R^5$ groups and wherein each $R^{12}$ and $R^{13}$ is independently selected from H, $C_1$–$C_6$ alkyl, —(CH$_2$)$_t$($C_3$–$C_{10}$ cycloalkyl), —(CH$_2$)$_t$($C_6$–$C_{10}$ aryl), —(CH$_2$)$_t$(5 to 10 membered heterocyclic), —(CH$_2$)$_t$O(CH$_2$)$_q$O$R^9$, —(CH$_2$)$_t$O$R^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

3. A compound of claim 2, wherein $R^{11}$ is —(CH$_2$)$_t$(5 to 10 membered heterocyclic), —C(O)N$R^{12}R^{13}$, —SO$_2$N$R^{12}R^{13}$ and —CO$_2$$R^{12}$, wherein t is an integer from 0 to 6, wherein said $R^{11}$ group —(CH$_2$)$_t$(5 to 10 membered heterocyclic) is optionally substituted by 1 to 5 $R^5$ groups and wherein each $R^{12}$ and $R^{13}$ is independently selected from H, $C_1$–$C_6$ alkyl, —(CH$_2$)$_t$($C_3$–$C_{10}$ cycloalkyl), —(CH$_2$)$_t$ ($C_6$–$C_{10}$ aryl), —(CH$_2$)$_t$(5 to 10 membered heterocyclic), —(CH$_2$)$_t$O(CH$_2$)$_q$O$R^9$, —(CH$_2$)$_t$O$R^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

4. A compound of claim 3, wherein $R^{11}$ is —(CH$_2$)$_t$(5 to 10 membered heterocyclic) and —C(O)N$R^{12}R^{13}$, wherein t is an integer from 0 to 6, wherein said $R^{11}$ group —(CH$_2$)$_t$(5 to 10 membered heterocyclic) is optionally substituted by 1 to 5 $R^5$ groups and wherein each $R^{12}$ and $R^{13}$ is independently selected from H, $C_1$–$C_6$ alkyl, —(CH$_2$)$_t$($C_3$–$C_{10}$ cycloalkyl), —(CH$_2$)$_t$($C_6$–$C_{10}$ aryl), —(CH$_2$)$_t$(5 to 10 membered heterocyclic), —(CH$_2$)$_t$O(CH$_2$)$_q$O$R^9$, —(CH$_2$)$_t$O$R^9$, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

5. A compound of claim 4, wherein $R^{11}$ is —C(O)$NR^{12}R^{13}$, wherein $R^{12}$ and $R^{13}$ are independently selected from H, $C_1$–$C_6$ alkyl, —$(CH_2)_t(C_3$–$C_{10}$ cycloalkyl), —$(CH_2)_t(C_6$–$C_{10}$ aryl), —$(CH_2)_t$(5 to 10 membered heterocyclic), —$(CH_2)_tO(CH_2)_qOR^9$, —$(CH_2)_tOR^9$, wherein t is an integer from 0 to 6, q is an integer from 2 to 6, and the alkyl, aryl and heterocyclic moieties of the foregoing $R^{12}$ and $R^{13}$ groups are optionally substituted by 1 to 3 substituents independently selected from $R^5$ or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents, with the proviso $R^{12}$ and $R^{13}$ are not both bonded to the nitrogen directly through an oxygen.

6. A compound of claim 5, wherein $R^{11}$ is —C(O)$NR^{12}R^{13}$, wherein $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl. azetidinyl, pyrrolidinyl, piperidinyl, piperazinyl, morpholinyl, thiomorpholinyl, isoquinolinyl, or dihydroisoquinolinyl ring are optionally substituted by 1 to 5 $R^5$ substituents.

7. A compound of claim 6, wherein $R^{11}$ is —C(O)$NR^{12}R^{13}$, wherein $R^{12}$ and $R^{13}$ are taken together with the nitrogen to which they are attached to form a pyrrolidinyl, piperidinyl, piperazinyl, morpholinyl, thiomorpholinyl, isoquinolinyl, or dihydroisoquinolinyl ring, wherein said pyrrolidinyl, piperidinyl, piperazinyl, morpholinyl, thiomorpholinyl, isoquinolinyl, or dihydroisoquinolinyl ring are optionally substituted by 1 to 5 $R^5$ substituents.

8. A compound of claim 7, wherein $R^{11}$ is —C(O)$NR^{12}R^{13}$, wherein $R^{12}$ and $R^{13}$ are taken together with the nitrogen to which they are attached to form a pyrrolidinyl, piperidinyl, piperazinyl, morpholinyl, or thiomorpholinyl ring, wherein said pyrrolidinyl, piperidinyl, piperazinyl, morpholinyl, or thiomorpholinyl ring are optionally substituted by 1 to 5 $R^5$ substituents.

9. A compound of claim 8, wherein $R^{11}$ is —C(O)$NR^{12}R^{13}$, wherein $R^{12}$ and $R^{13}$ are taken together with the nitrogen to which they are attached to form a pyrrolidinyl or piperidinyl ring, wherein said pyrrolidinyl or piperidinyl ring are optionally substituted by 1 to 5 $R^5$ substituents.

10. A compound of claim 9, wherein $R^{11}$ is —C(O)$NR^{12}R^{13}$, wherein $R^{12}$ and $R^{13}$ are taken together with the nitrogen to which they are attached to form a pyrrolidinyl ring, wherein said pyrrolidinyl is optionally substituted by 1 to 5 $R^5$ substituents.

11. A compound of claim 10, wherein $R^{11}$ is —C(O)$NR^{12}R^{13}$, wherein $R^{12}$ and $R^{13}$ are taken together with the nitrogen to which they are attached to form a pyrrolidin-1-yl ring, wherein said pyrrolidin-1-yl is optionally substituted by 1 to 5 $R^5$ substituents.

12. A compound of claim 4, wherein $R^{11}$ is —$(CH_2)_t$(5 to 10 membered heterocyclic) group, wherein t is an integer from 0 to 6, said —$(CH_2)_t$(5 to 10 membered heterocyclic) group is optionally substituted by 1 to 5 $R^5$ groups.

13. A compound of claim 12, wherein $R^{11}$ is —$(CH_2)_t$(5–8 membered heterocyclic) group, wherein t is an integer from 0 to 6, said —$(CH_2)_t$(5–8 membered heterocyclic) group is optionally substituted by 1 to 5 $R^5$ groups.

14. A compound of claim 13, wherein $R^{11}$ is —$(CH_2)_t$(5 or 6 membered heterocyclic) group, wherein t is an integer from 0 to 6, said —$(CH_2)_t$(5 or 6 membered heterocyclic) group is optionally substituted by 1 to 5 $R^5$ groups.

15. A compound of claim 14, wherein $R^{11}$ is —$(CH_2)_t$(5 membered heterocyclic) group, wherein t is an integer from 0 to 6, said —$(CH_2)_t$(5 membered heterocyclic) group is optionally substituted by 1 to 5 $R^5$ groups.

16. A compound of claim 15, wherein $R^{11}$ is —$(CH_2)_t$thiazolyl, wherein t is an integer from 0 to 6, said —$(CH_2)_t$thiazolyl is optionally substituted by 1 to 5 $R^5$ groups.

17. A compound of claim 1, wherein $R^1$ is a group of the formula

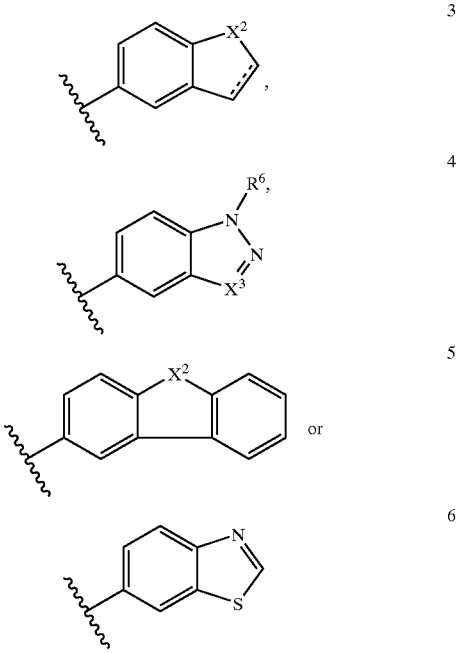

wherein $X^2$ is —S— or —N($R^6$)—, $X^3$ is N or CH, the dashed line in formula 3 represents an optional double bond, and the above $R^1$ groups of formulas 3 and 5 are optionally substituted by 1 to 5 $R^5$ substituents and the $R^1$ groups of formulas 4 and 6 are optionally substituted by 1 to 3 $R^5$ substituents.

18. A compound of claim 17 wherein $R^1$ is a group of formula 3 above wherein said group is optionally substituted by 1 to 5 $R^5$ substituents.

19. A compound of claim 1 wherein said compound is selected from the group consisting of (3R)-(3-methoxy-pyrrolidin-1-yl)-[7-(2-methyl-1H-indol-5-yloxy)-thieno[3,2-b]pyridin-2-yl]-methanone;

(3S)-(3-Methoxy-pyrrolidin-1-yl)-[7-(2-methyl-1H-indol-5-yloxy)-thieno[3,2-b]pyridin-2-yl]-methanone;

(3R,4R)-(3,4-Dimethoxy-pyrrolidin-1-yl)-[7-(2-methyl-1H-indol-5-yloxy)-thieno[3,2-b]pyridin-2-yl]-methanone;

meso-(3,4-Dimethoxy-pyrrolidin-1-yl)-[7-(2-methyl-1H-indol-5-yloxy)-thieno[3,2-b]pyridin-2-yl]-methanone;

(3S,4S)-(3,4-Dimethoxy-pyrrolidin-1-yl)-[7-(2-methyl-1H-indol-5-yloxy)-thieno[3,2-b]pyridin-2-yl]-methanone;

(R)-(2-Hydroxymethyl-pyrrolidin-1-yl)-[7-(2-methyl-1H-indol-5-yloxy)-thieno[3,2-b]pyridin-2-yl]-methanone;

(S)-(2-Hydroxymethyl-pyrrolidin-1-yl)-[7-(2-methyl-1H-indol-5-yloxy)-thieno[3,2-b]pyridin-2-yl]-methanone;

(2R)-(2-Methoxymethyl-pyrrolidin-1-yl)-[7-(2-methyl-1H-indol-5-yloxy)-thieno[3,2-b]pyridin-2-yl]-methanone;

(2S)-(2-Methoxymethyl-pyrrolidin-1-yl)-[7-(2-methyl-1H-indol-5-yloxy)-thieno[3,2-b]pyridin-2-yl]-methanone;

(R)-[7-(1-Ethyl-2-methyl-1H-indol-5-yloxy)-thieno[3,2-b]pyridin-2-yl]-(2-methoxymethyl-pyrrolidin-1-yl)-methanone;

(2R)-[7-(1,2-Dimethyl-1H-indol-5-yloxy)-thieno[3,2-b]pyridin-2-yl]-(2-methoxymethyl-pyrrolidin-1-yl)-methanone;

(2R)-1-{5-[2-(2-Methoxymethyl-pyrrolidine-1-carbonyl)-thieno[3,2-b]pyridin-7-yloxy]-2-methyl-indol-1-yl}-ethanone;

(2R)-[7-(1-Methanesulfonyl-2-methyl-1H-indol-5-yloxy)-thieno[3,2-b]pyridin-2-yl]-(2-methoxymethyl-pyrrolidin-1-yl)-methanone;

2-(3-Methyl-3H-imidazol-4-yl)-7-(2-methyl-1H-indol-5-yloxy)-thieno[3,2-b]pyridine;

2-(1-Methyl-1H-imidazol-2-yl)-7-(2-methyl-1H-indol-5-yloxy)-thieno[3,2-b]pyridine;

2-{2-[7-(2-Methyl-1H-indol-5-yloxy)-thieno[3,2-b]pyridin-2-yl]-thiazol-4-yl}-propan-2-ol;

2-{2-[7-(2-Methyl-quinolin-6-yloxy)-thieno[3,2-b]pyridin-2-yl]-thiazol-4-yl}-propan-2-ol;

2-{2-[7-(Quinolin-6-yloxy)-thieno[3,2-b]pyridin-2-yl]-thiazol-4-yl}-propan-2-ol;

2-{2-[7-(1-Methyl-5-trifluoromethyl-1H-pyrazol-3-yloxy)-thieno[3,2-b]pyridin-2-yl]thiazol-4-yl}-propan-2-ol;

4-Methyl-2-[7-(2-methyl-1H-indol-5-yloxy)-thieno[3,2-b]pyridin-2-yl]-thiazol-5-yl}-(4-methyl-piperazin-1-yl)-methanone;

2-Methyl-5-{2-[4-methyl-5-(4-methyl-piperazine-1-carbonyl)-thiazol-2-yl]-thieno[3,2-b]pyridin-7-yloxy}1H-indole-3-carbonitrile;

{4-Methyl-2-[7-(5-phenyl-1H-pyrazol-3-yloxy)-thieno[3,2-b]pyridin-2-yl]-thiazol-5-yl}-morpholin-4-yl-methanone;

(2-{7-[5-(4-Fluoro-phenyl)-1H-pyrazol-3-yloxy]-thieno[3,2-b]pyridin-2-yl}-4-methyl-thiazol-5-yl)-(4-methyl-piperazin-1-yl)-methanone;

2-{7-[5-(4-Methoxy-phenyl)-1H-pyrazol-3-yloxy]-thieno[3,2-b]pyridin-2-yl}-4-methyl-thiazol-5-yl)-(4-methyl-piperazin-1-yl)-methanone; and pharmaceutically acceptable salts and solvates of said compounds.

20. A compound of the formula 25 or 26

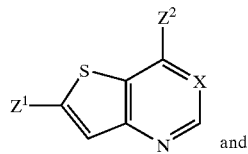

and

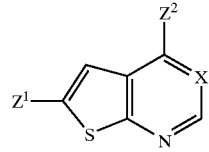

or a pharmaceutically acceptable salt or solvate thereof, wherein:

$Z^1$ is halo, —$CO_2H$, —$CONH_2$, $CSNH_2$ and $Z^2$ is —$OR^1$;
X is CH;
wherein $R^1$ is $C_1$–$C_6$ alkyl, —$C(O)(C_1$–$C_6$ alkyl), $C_6$–$C_{10}$ aryl or 5 to 13 membered heterocyclic, wherein said $C_6$–$C_{10}$ aryl and 5 to 13 membered heterocyclic groups are optionally substituted by 1 to 5 $R^5$ substituents;

each $R^5$ is independently selected from halo, cyano, nitro, trifluoromethoxy, trifluoromethyl, azido, —$C(O)R^8$, —$C(O)OR^8$, —$OC(O)R^8$, —$OC(O)OR^8$, —$NR^6C(O)R^7$, —$C(O)NR^6R^7$, —$NR^6R^7$, —$OR^9$, —$SO_2NR^6R^7$, $C_1$–$C_6$ alkyl, —$(CH_2)_jO(CH_2)_q NR^6R^7$, —$(CH_2)_jO(CH_2)_qOR^9$, —$(CH_2)_tOR^9$, —$S(O)_j(C_1$–$C_6$ alkyl), —$(CH_2)_t(C_6$–$C_{10}$ aryl), —$(CH_2)_t(5$ to $10$ membered heterocyclic), —$C(O)(CH_2)_t(C_6$–$C_{10}$ aryl), —$(CH_2)_tO(CH_2)_j(C_6$–$C_{10}$ aryl), —$(CH_2)_tO(CH_2)_q(5$ to $10$ membered heterocyclic), —$C(O)(CH_2)_t(5$ to $10$ membered heterocyclic), —$(CH_2)_jNR^7(CH_2)_qNR^6R^7$, —$(CH_2)_j NR^7CH_2C(O)NR^6R^7$, —$(CH_2)_jNR^7(CH_2)_qNR^9C(O)R^8$, —$(CH_2)_jNR^7(CH_2)_qOR^9$, —$(CH_2)_j NR^7(CH_2)_qS(O)_j(C_1$–$C_6$ alkyl), —$(CH_2)_jNR^7(CH_2)_tR^6$, —$SO_2(CH_2)_t(C_6$–$C_{10}$ aryl), and —$SO_2(CH_2)_t(5$ to $10$ membered heterocyclic), wherein j is an integer from 0 to 2, t is an integer from 0 to 6, q is an integer from 2 to 6, the —$(CH_2)_q$— and —$(CH_2)_t$— moieties of the foregoing $R^5$ groups optionally include a carbon-carbon double or triple bond where t is an integer between 2 and 6, and the alkyl, aryl and heterocyclic moieties of the foregoing $R^5$ groups are optionally substituted by 1 to 3 substituents independently selected from halo, cyano, nitro, trifluoromethyl, azido, —$C(O)R^8$, —$C(O)OR^8$, —$OC(O)R^8$, —$OC(O)OR^8$, —$NR^6C(O)R^7$, —$C(O)NR^6R^7$, —$(CH_2)_tNR^6R^7$, $C_1$–$C_6$ alkyl, —$(CH_2)_t(C_6$–$C_{10}$ aryl), —$(CH_2)_t(5$ to $10$ membered heterocyclic), —$(CH_2)_tO(CH_2)_qOR^9$, and —$(CH_2)_tOR^9$, wherein t is an integer from 0 to 6 and q is an integer from 2 to 6;

each $R^6$ and $R^7$ is independently selected from H, $C_1$–$C_6$ alkyl, —$(CH_2)_t(C_6$–$C_{10}$ aryl), —$(CH_2)_t(5$ to $10$ membered heterocyclic), —$(CH_2)_tO(CH_2)_qOR^9$, and —$(CH_2)_tOR^9$, wherein t is an integer from 0 to 6 and q is an integer from 2 to 6, and the alkyl, aryl and heterocyclic moieties of the foregoing $R^6$ and $R^7$ groups are optionally substituted by 1 to 3 substituents independently selected from halo, cyano, nitro, trifluoromethyl, azido, —C(O)R$^8$, —C(O)OR$^8$, —CO(O)R$^8$, —OC(O)OR$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, with the proviso that where R$^6$ and R$^7$ are both attached to the same nitrogen, then R$^6$ and R$^7$ are not both bonded to the nitrogen directly through an oxygen;

each R$^8$ is independently selected from H, C$_1$–C$_{10}$ alkyl, —(CH$_2$)$_t$(C$_6$–C$_{10}$ aryl), and —(CH$_2$)$_t$(5 to 10 membered heterocyclic), wherein t is an integer from 0 to 6;

each R$^9$ and R$^{10}$ is independently selected from H and C$_1$–C$_6$ alkyl; and R$^{11}$ is H, C$_1$–C$_6$ alkyl, —C(O)NR$^{12}$R$^{13}$, —C(O)(C$_6$–C$_{10}$ aryl), —(CH$_2$)$_t$(C$_6$–C$_{10}$ aryl), —(CH$_2$)$_t$(5 to 10 membered heterocyclic), —(CH$_2$)$_t$NR$^{12}$R$^{13}$, —SO$_2$NR$^{12}$R$^{13}$ and —CO$_2$R$^{12}$, wherein t is an integer from 0 to 6, wherein said R$^{11}$ groups C$_1$–C$_6$ alkyl, —C(O)(C$_6$–C$_{10}$ aryl), —(CH$_2$)$_t$(C$_6$–C$_{10}$ aryl), and —(CH$_2$)$_t$(5 to 10 membered heterocyclic) are optionally substituted by 1 to 5 R$^5$ groups, and wherein each R$^{12}$ and R$^{13}$ is independently selected from H, C$_1$–C$_6$ alkyl, —(CH$_2$)$_t$(C$_3$–C$_{10}$ cycloalkyl), —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, —(CH$_2$)$_t$OR$^9$, q is an integer from 2 to 6, and the alkyl, aryl and heterocyclic moieties of the foregoing R$^{12}$ and R$^{13}$ groups are optionally substituted by 1 to 3 substituents independently selected from R$^5$ or R$^{12}$ and R$^{13}$ taken together with the nitrogen to which they are attached to form a C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said C$_5$–C$_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are optionally substituted by 1 to 5 R$^5$ substituents, with the proviso R$^{12}$ and R$^{13}$ are not both bonded to the nitrogen directly through an oxygen.

21. A pharmaceutical composition which comprises a therapeutically effective amount of a compound of claim 1 and a pharmaceutically acceptable carrier.

* * * * *